United States Patent
Stepic et al.

(10) Patent No.: US 10,966,441 B1
(45) Date of Patent: Apr. 6, 2021

(54) REFRIGERATION/COLD STORAGE FOOD SAFETY FILTERS

(71) Applicants: Roger W. Stepic, Lutz, FL (US); Rebecca W. Stepic, Lutz, FL (US)

(72) Inventors: Roger W. Stepic, Lutz, FL (US); Rebecca W. Stepic, Lutz, FL (US)

(*) Notice: Subject to any disclaimer, the term of this patent is extended or adjusted under 35 U.S.C. 154(b) by 88 days.

(21) Appl. No.: 15/953,709

(22) Filed: Apr. 16, 2018

Related U.S. Application Data

(60) Provisional application No. 62/485,636, filed on Apr. 14, 2017.

(51) Int. Cl.
| | |
|---|---|
| *A01N 65/00* | (2009.01) |
| *A01N 65/03* | (2009.01) |
| *A23L 3/3427* | (2006.01) |
| *A01N 65/12* | (2009.01) |
| *A01N 65/16* | (2009.01) |
| *A01N 65/48* | (2009.01) |
| *A61L 9/013* | (2006.01) |
| *B01D 53/02* | (2006.01) |
| *A23L 3/36* | (2006.01) |
| *B01D 53/84* | (2006.01) |
| *A61L 9/014* | (2006.01) |
| *A01N 65/10* | (2009.01) |
| *A01N 65/20* | (2009.01) |
| *A01N 65/36* | (2009.01) |
| *A01N 65/08* | (2009.01) |

(52) U.S. Cl.
CPC ............ *A23L 3/3427* (2013.01); *A01N 65/00* (2013.01); *A01N 65/03* (2013.01); *A01N 65/08* (2013.01); *A01N 65/10* (2013.01); *A01N 65/12* (2013.01); *A01N 65/16* (2013.01); *A01N 65/20* (2013.01); *A01N 65/36* (2013.01); *A01N 65/48* (2013.01); *A23L 3/36* (2013.01); *A61L 9/013* (2013.01); *A61L 9/014* (2013.01); *B01D 53/02* (2013.01); *B01D 53/84* (2013.01); *A23V 2002/00* (2013.01); *A61L 2209/14* (2013.01); *B01D 2253/20* (2013.01); *B01D 2257/80* (2013.01); *B01D 2259/4525* (2013.01)

(58) Field of Classification Search
None
See application file for complete search history.

(56) References Cited

U.S. PATENT DOCUMENTS

| | | | |
|---|---|---|---|
| 3,935,363 A | 1/1976 | Burkholder et al. | |
| 4,384,972 A | 5/1983 | Nakamura et al. | |
| 5,885,481 A | 3/1999 | Venkateshwaran et al. | |
| 6,139,935 A | 10/2000 | Cullen et al. | |
| 6,244,432 B1 | 6/2001 | Saari et al. | |
| 6,508,955 B1 | 1/2003 | DelDuca et al. | |
| 6,921,026 B2 | 7/2005 | Saari et al. | |
| 7,175,741 B2 | 2/2007 | West et al. | |
| 8,057,586 B2 | 11/2011 | Powers et al. | |
| 8,210,939 B2 | 7/2012 | Norton et al. | |
| 8,486,854 B2 | 7/2013 | Berrada et al. | |
| 8,617,295 B2 * | 12/2013 | Billingsley | B01D 39/06 422/169 |
| 2003/0060555 A1 | 3/2003 | Lorah et al. | |
| 2003/0194516 A1 | 10/2003 | Payne et al. | |
| 2004/0224144 A1 | 11/2004 | Saari et al. | |
| 2007/0175330 A1 | 8/2007 | Barone et al. | |
| 2009/0163887 A1 * | 6/2009 | Arehart | A61F 13/8405 604/359 |
| 2010/0176044 A1 * | 7/2010 | Domb | B01J 20/0229 210/205 |
| 2013/0071639 A1 * | 3/2013 | Larsson | E04F 13/002 428/213 |
| 2014/0261475 A1 * | 9/2014 | Kizer | A24D 3/066 131/275 |
| 2015/0082556 A1 * | 3/2015 | Medoff | D04H 1/42 8/444 |
| 2017/0361306 A1 * | 12/2017 | Wang | B01D 37/025 |

OTHER PUBLICATIONS

Parashar et al. (Antimicrobial and Antioxidant Activities of Fruits and Vegetable Peels: A review) (Year: 2014).*

* cited by examiner

*Primary Examiner* — Sarah Alawadi
(74) *Attorney, Agent, or Firm* — Michele L. Lawson; Smith & Hopen, P.A.

(57) ABSTRACT

A food-grade, all-natural cold storage anti-bacterial filter is disclosed. The filter may control moisture, gaseous contaminates, mold, and bacteria within a cold storage unit; improve food safety; and improve the life of cold storage equipment. Reduced food spoilage, reduced energy usage, and increased cold storage shelf life may result from use of the filter. The filter includes a mixture of effective amounts of a base mineral, hygroscopic plant botanicals, and anti-bacterial plant botanicals, wherein the mixture is disposed in an FDA-approved food grade material.

16 Claims, 15 Drawing Sheets

Filters absorb moisture

Filters release moisture

Premier All Natural Filters Test Data - 2004 vs 2005

| Site # | Vendor Name | 2004 Bill End | 2004 Bill Amt | 2004 Daily Amt | 2005 Bill End | 2005 Bill Amt | 2005 Daily Amt | Bill Diff | Daily Amt Diff | Diff x 28 Days |
|---|---|---|---|---|---|---|---|---|---|---|
| | Teco Tampa Electric Company | 02/05/04 | 2,204.18 | 78.72 | 02/07/05 | 2,108.22 | 68.01 | (95.96) | (10.71) | (299.88) |
| | Teco Tampa Electric Company | 03/05/04 | 2,599.29 | 89.63 | 03/07/05 | 2,188.34 | 78.15 | (410.95) | (11.48) | (321.44) |
| | Teco Tampa Electric Company | 04/06/04 | 2,705.48 | 84.55 | 04/08/05 | 2,515.87 | 83.86 | (189.61) | (0.69) | (19.32) |
| | Teco Tampa Electric Company | 05/07/04 | 2,854.47 | 92.08 | 05/05/05 | 2,487.72 | 85.78 | (366.75) | (6.30) | (176.40) |
| | Teco Tampa Electric Company | 06/08/04 | 3,178.49 | 99.33 | 06/07/05 | 3,012.84 | 91.30 | (165.65) | (8.03) | (224.84) |
| | Teco Tampa Electric Company | 07/08/04 | 3,125.53 | 104.18 | 07/05/05 | 2,948.83 | 105.32 | (176.70) | 1.14 | 31.92 |
| #1 | | | 16,667.44 | | | 15,261.82 | | (1,405.62) | | (1,019.96) |
| | City of Clearwater, FL | 01/20/04 | 292.26 | 9.13 | 01/21/05 | 249.47 | 8.05 | (42.79) | (1.08) | (30.24) |
| | City of Clearwater, FL | 02/18/04 | 151.78 | 5.06 | 02/17/05 | 251.63 | 9.32 | 99.85 | 4.26 | 119.30 |
| | City of Clearwater, FL | 03/19/04 | 271.79 | 9.37 | 03/23/05 | 300.92 | 9.40 | 29.13 | 0.03 | 0.84 |
| | City of Clearwater, FL | 04/21/04 | 290.01 | 8.79 | 04/21/05 | 332.59 | 10.73 | 42.58 | 1.94 | 54.32 |
| | City of Clearwater, FL | 05/20/04 | 263.18 | 9.08 | 05/20/05 | 281.84 | 9.72 | 18.66 | 0.64 | 17.92 |
| | City of Clearwater, FL | 06/22/04 | 289.43 | 8.77 | 06/21/05 | 306.73 | 9.59 | 17.30 | 0.82 | 22.96 |
| | Progress Energy/Florida Power Corp | 02/09/04 | 1,402.43 | 45.24 | 02/04/05 | 1,409.97 | 48.62 | 7.54 | 3.38 | 94.64 |
| | Progress Energy/Florida Power Corp | 03/09/04 | 1,375.32 | 47.42 | 03/08/05 | 1,643.77 | 51.37 | 268.45 | 3.95 | 110.60 |
| | Progress Energy/Florida Power Corp | 04/07/04 | 1,373.94 | 47.38 | 04/08/05 | 1,744.59 | 56.28 | 370.65 | 8.90 | 249.20 |
| | Progress Energy/Florida Power Corp | 05/07/04 | 1,708.85 | 56.96 | 05/07/05 | 1,844.11 | 63.59 | 135.26 | 6.63 | 185.64 |
| | Progress Energy/Florida Power Corp | 06/08/04 | 2,079.75 | 64.99 | 06/06/05 | 2,028.04 | 67.60 | (51.71) | 2.61 | 73.08 |
| | Progress Energy/Florida Power Corp | 07/08/04 | 2,067.97 | 68.93 | 07/08/05 | 2,201.56 | 73.38 | 133.59 | 4.45 | 124.60 |
| #2 | | | 11,566.71 | | | 12,595.22 | | 1,028.51 | | 1,022.86 |
| | Teco Tampa Electric Company | 02/06/04 | 1,610.60 | 57.52 | 02/08/05 | 1,844.30 | 59.49 | 233.70 | 1.97 | 55.16 |
| | Teco Tampa Electric Company | 03/08/04 | 1,877.09 | 60.55 | 03/09/05 | 1,722.76 | 59.41 | (154.33) | (1.14) | (31.92) |
| | Teco Tampa Electric Company | 04/07/04 | 1,783.54 | 59.45 | 04/07/05 | 1,860.36 | 64.15 | 76.82 | 4.70 | 131.60 |
| | Teco Tampa Electric Company | 05/10/04 | 2,133.17 | 64.64 | 05/07/05 | 1,915.22 | 63.84 | (217.95) | (0.80) | (22.40) |
| | Teco Tampa Electric Company | 06/08/04 | 2,197.42 | 75.77 | 06/07/05 | 2,178.38 | 70.27 | (19.04) | (5.50) | (154.00) |
| | Teco Tampa Electric Company | 07/08/04 | 2,336.89 | 77.90 | 07/08/05 | 2,370.81 | 76.48 | 33.92 | (1.42) | (39.76) |
| #3 | | | 11,938.71 | | | 11,891.83 | | (46.88) | | (61.32) |

FIG. 11

| | | | | | | | |
|---|---|---|---|---|---|---|---|
| | City of Clearwater, FL | 02/23/04 | 53.92 | 1.69 | 02/18/05 | 39.15 | 1.63 | (14.77) | (0.06) | (1.68) |
| | City of Clearwater, FL | 03/22/04 | 47.88 | 1.71 | 03/24/05 | 57.27 | 1.68 | 9.39 | (0.03) | (0.84) |
| | City of Clearwater, FL | 04/22/04 | 54.08 | 1.74 | 04/25/05 | 53.33 | 1.67 | (0.75) | (0.07) | (1.96) |
| | City of Clearwater, FL | 05/24/04 | 53.46 | 1.67 | 05/25/05 | 46.30 | 1.54 | (7.16) | (0.13) | (3.64) |
| | City of Clearwater, FL | 06/24/04 | 53.26 | 1.72 | 06/23/05 | 43.21 | 1.49 | (10.05) | (0.23) | (6.44) |
| | Progress Energy/Florida Power Corp | 02/20/04 | 1,749.55 | 60.33 | 02/18/05 | 1,542.61 | 53.19 | (206.94) | (7.14) | (199.90) |
| | Progress Energy/Florida Power Corp | 03/19/04 | 1,857.70 | 64.06 | 03/19/05 | 1,569.19 | 54.11 | (288.51) | (9.95) | (278.60) |
| | Progress Energy/Florida Power Corp | 04/19/04 | 2,074.42 | 66.92 | 04/20/05 | 1,959.48 | 61.23 | (114.94) | (5.69) | (159.32) |
| | Progress Energy/Florida Power Corp | 05/20/04 | 2,381.93 | 79.40 | 05/19/05 | 1,950.67 | 67.26 | (431.26) | (12.14) | (339.85) |
| | Progress Energy/Florida Power Corp | 06/17/04 | 2,499.06 | 86.17 | 06/29/05 | 2,356.80 | 73.65 | (142.26) | (12.52) | (350.56) |
| #4 | | | 10,825.26 | | | 9,618.01 | | (1,207.25) | | (1,342.80) |
| | Teco Tampa Electric Company | 02/22/05 | 2,179.88 | 75.17 | 02/22/05 | 1,876.43 | 64.70 | (303.45) | (10.47) | (293.16) |
| | Teco Tampa Electric Company | 03/23/04 | 2,366.46 | 73.95 | 03/22/05 | 1,869.57 | 66.77 | (496.89) | (7.18) | (281.04) |
| | Teco Tampa Electric Company | 04/22/04 | 2,463.39 | 82.11 | 04/22/05 | 2,195.59 | 70.83 | (267.80) | (11.28) | (315.84) |
| | Teco Tampa Electric Company | 05/21/05 | 2,503.81 | 89.42 | 05/21/05 | 2,249.47 | 77.57 | (254.34) | (11.85) | (331.80) |
| | Teco Tampa Electric Company | 06/22/04 | 2,608.50 | 89.95 | 06/22/05 | 2,709.66 | 84.68 | 101.16 | (5.27) | (147.56) |
| #5 | | | 12,122.04 | | | 10,900.72 | | (1,221.32) | | (1,289.40) |

FIG. 11 (cont'd)

| | | | | | | | |
|---|---|---|---|---|---|---|---|
| Teco Tampa Electric Company | 02/12/04 | 1,775.87 | 61.24 | 02/11/05 | 1,654.62 | 53.37 | (121.25) | (7.87) | (220.36) |
| Teco Tampa Electric Company | 03/15/04 | 2,020.56 | 63.14 | 03/12/05 | 1,590.59 | 54.85 | (429.97) | (8.29) | (232.12) |
| Teco Tampa Electric Company | 04/14/04 | 1,974.29 | 65.81 | 04/12/05 | 1,885.06 | 60.81 | (89.23) | (5.00) | (140.00) |
| Teco Tampa Electric Company | 05/13/04 | 2,103.83 | 72.55 | 05/12/05 | 1,700.45 | 56.68 | (403.38) | (15.87) | (444.36) |
| Teco Tampa Electric Company | 06/14/04 | 2,437.74 | 76.18 | 06/13/05 | 2,104.00 | 65.75 | (333.74) | (10.43) | (292.04) |
| Teco Tampa Electric Company | 07/14/04 | 2,374.62 | 79.15 | 07/13/05 | 2,191.49 | 73.05 | (183.13) | (6.10) | (178.80) |
| #6 | | 12,686.91 | | | 11,126.21 | | (1,560.70) | | (1,499.68) |
| Teco Tampa Electric Company | 02/16/04 | 1,938.01 | 62.52 | 02/16/05 | 1,936.79 | 64.56 | (1.22) | 2.04 | 57.12 |
| Teco Tampa Electric Company | 03/17/04 | 1,936.00 | 64.53 | 03/17/05 | 1,969.86 | 67.93 | 33.86 | 3.40 | 95.20 |
| Teco Tampa Electric Company | 04/16/04 | 2,028.35 | 67.61 | 04/18/05 | 2,244.30 | 70.13 | 215.95 | 2.52 | 70.56 |
| Teco Tampa Electric Company | 05/18/04 | 2,275.05 | 71.10 | 05/17/05 | 2,063.14 | 71.14 | (211.91) | 0.04 | 1.12 |
| Teco Tampa Electric Company | 06/17/04 | 2,398.74 | 79.96 | 06/16/05 | 2,337.95 | 77.93 | (60.79) | (2.03) | (56.84) |
| Teco Tampa Electric Company | 07/19/04 | 2,478.39 | 77.45 | 07/18/05 | 2,561.54 | 80.05 | 83.15 | 2.60 | 72.80 |
| #7 | | 13,054.54 | | | 13,113.58 | | 59.04 | | 239.96 |
| Progress Energy/Florida Power Corp | 02/11/04 | 1,433.27 | 49.42 | 02/09/05 | 1,434.45 | 49.46 | 1.18 | 0.04 | 1.12 |
| Progress Energy/Florida Power Corp | 03/11/04 | 1,497.00 | 51.62 | 03/11/05 | 1,453.20 | 48.44 | (43.80) | (3.18) | (89.04) |
| Progress Energy/Florida Power Corp | 04/12/04 | 1,756.09 | 54.88 | 04/11/05 | 1,716.50 | 55.37 | (39.59) | 0.49 | 13.72 |
| Progress Energy/Florida Power Corp | 05/10/04 | 1,788.59 | 63.88 | 05/11/05 | 1,845.19 | 61.51 | 56.60 | (2.37) | (66.36) |
| Progress Energy/Florida Power Corp | 06/10/04 | 2,286.49 | 73.76 | 06/09/05 | 2,023.88 | 69.79 | (262.61) | (3.97) | (111.16) |
| Progress Energy/Florida Power Corp | 07/12/04 | 2,388.03 | 74.63 | 07/11/05 | 2,335.98 | 73.00 | (52.05) | (1.63) | (45.64) |
| #8 | | 11,149.47 | | | 10,809.20 | | (340.27) | | (297.36) |

FIG. 11 (cont'd)

| | | | | | | | |
|---|---|---|---|---|---|---|---|
| | Teco Tampa Electric Company | 02/25/04 | 2,034.25 | 67.81 | 02/24/05 | 2,260.54 | 75.35 | 226.29 | 7.54 | 211.12 |
| | Teco Tampa Electric Company | 03/26/04 | 2,070.44 | 69.01 | 03/24/05 | 2,221.78 | 79.35 | 153.34 | 10.34 | 289.52 |
| | Teco Tampa Electric Company | 04/27/04 | 2,301.19 | 71.91 | 04/25/05 | 2,511.29 | 78.48 | 210.10 | 6.57 | 183.96 |
| | Teco Tampa Electric Company | 05/26/04 | 2,417.66 | 83.37 | 05/25/05 | 2,483.46 | 82.78 | 65.80 | (0.59) | (16.52) |
| | Teco Tampa Electric Company | 06/25/04 | 2,889.08 | 96.30 | 06/24/05 | 2,772.29 | 92.41 | (116.79) | (3.89) | (108.92) |
| #9 | | | 11,712.62 | | | 12,249.36 | | 536.74 | | 559.16 |
| | Teco Tampa Electric Company | 02/06/04 | 1,695.35 | 60.55 | 02/07/05 | 1,871.66 | 62.39 | 176.31 | 1.84 | 51.52 |
| | Teco Tampa Electric Company | 02/08/04 | 358.68 | 13.57 | 02/08/05 | 352.46 | 12.15 | (6.22) | 0.58 | 16.24 |
| | Teco Tampa Electric Company | 03/09/04 | 2,123.79 | 66.37 | 03/08/05 | 1,699.26 | 58.59 | (424.53) | (7.78) | (217.84) |
| | Teco Tampa Electric Company | 03/10/04 | 358.68 | 13.96 | 03/09/05 | 352.46 | 12.15 | (6.22) | 0.19 | 5.32 |
| | Teco Tampa Electric Company | 04/07/04 | 2,019.93 | 69.65 | 04/08/05 | 1,897.08 | 61.20 | (122.85) | (8.45) | (236.60) |
| | Teco Tampa Electric Company | 04/08/04 | 358.68 | 12.37 | 04/08/05 | 352.46 | 11.75 | (6.22) | (0.62) | (17.36) |
| | Teco Tampa Electric Company | 05/10/04 | 358.68 | 11.21 | 05/09/05 | 352.46 | 60.82 | (6.22) | 49.61 | 1,389.08 |
| | Teco Tampa Electric Company | 05/10/04 | 2,311.47 | 70.04 | 05/07/05 | 1,763.65 | 11.37 | (547.82) | (58.67) | (1,642.76) |
| | Teco Tampa Electric Company | 06/08/04 | 2,333.00 | 80.45 | 06/08/05 | 2,090.85 | 65.34 | (242.15) | (15.11) | (423.08) |
| | Teco Tampa Electric Company | 06/08/04 | 358.68 | 13.96 | 06/08/05 | 352.46 | 11.75 | (6.22) | (0.21) | (5.88) |
| | Teco Tampa Electric Company | 07/08/04 | 2,508.90 | 83.63 | 07/08/05 | 2,095.25 | 69.84 | (413.65) | (13.79) | (386.12) |
| | Teco Tampa Electric Company | 07/08/04 | 358.68 | 13.96 | 07/08/05 | 352.46 | 11.75 | (6.22) | (0.21) | (5.88) |
| #10 | | | 15,144.52 | | | 13,532.51 | | (1,612.01) | | (1,473.36) |
| | Teco Tampa Electric Company | 02/13/04 | 2,343.18 | 80.80 | 02/14/05 | 2,451.83 | 74.30 | 108.65 | (6.50) | (182.00) |
| | Teco Tampa Electric Company | 03/15/04 | 2,375.93 | 76.64 | 03/15/05 | 2,472.34 | 85.25 | 96.41 | 8.61 | 241.08 |
| | Teco Tampa Electric Company | 04/15/04 | 2,527.92 | 81.55 | 04/14/05 | 2,676.84 | 89.23 | 148.92 | 7.68 | 215.04 |
| | Teco Tampa Electric Company | 05/15/04 | 2,739.86 | 91.33 | 05/13/05 | 2,517.96 | 86.83 | (221.90) | (4.50) | (126.00) |
| | Teco Tampa Electric Company | 06/14/04 | 3,083.85 | 102.79 | 06/14/05 | 3,057.81 | 95.56 | (26.04) | (7.23) | (202.44) |
| | Teco Tampa Electric Company | 07/15/04 | 3,168.19 | 102.20 | 07/14/05 | 3,131.48 | 104.38 | (36.71) | 2.18 | 61.04 |
| #11 | | | 16,238.93 | | | 16,308.26 | | 69.33 | | 6.72 |

FIG. 11 (cont'd)

| | | | | | | | | |
|---|---|---|---|---|---|---|---|---|
| Progress Energy/Florida Power Corp | 02/18/05 | 1,937.22 | 66.80 | 02/16/05 | 1,717.45 | 61.34 | (219.77) | (5.46) | (152.88) |
| Progress Energy/Florida Power Corp | 03/19/04 | 2,124.30 | 70.81 | 03/17/05 | 1,790.78 | 61.75 | (333.52) | (9.06) | (253.68) |
| Progress Energy/Florida Power Corp | 04/20/04 | 2,178.17 | 68.07 | 04/18/05 | 2,224.39 | 69.51 | 46.22 | 1.44 | 40.32 |
| Progress Energy/Florida Power Corp | 05/18/05 | 2,228.65 | 79.59 | 05/16/05 | 2,144.61 | 76.59 | (84.04) | (3.00) | (84.00) |
| Progress Energy/Florida Power Corp | 06/18/04 | 2,722.09 | 87.81 | 06/17/05 | 2,786.22 | 87.07 | 64.13 | (0.74) | (20.72) |
| #12 | | 11,190.43 | | | 10,663.45 | | (526.98) | | (470.96) |
| Teco Tampa Electric Company | 02/22/05 | 2,151.87 | 74.20 | 02/21/05 | 2,013.55 | 62.92 | (138.32) | (11.28) | (315.84) |
| Teco Tampa Electric Company | 03/22/04 | 2,358.30 | 76.07 | 03/21/05 | 1,878.49 | 67.09 | (479.81) | (8.98) | (251.44) |
| Teco Tampa Electric Company | 04/22/04 | 2,338.12 | 75.42 | 04/21/05 | 2,151.30 | 69.40 | (186.82) | (6.02) | (168.56) |
| Teco Tampa Electric Company | 05/21/05 | 2,341.64 | 80.75 | 05/20/05 | 2,090.18 | 72.07 | (251.46) | (8.68) | (243.04) |
| Teco Tampa Electric Company | 06/22/04 | 2,793.59 | 87.30 | 06/21/05 | 2,451.80 | 76.62 | (341.79) | (10.68) | (299.04) |
| #13 | | 11,983.52 | | | 10,585.32 | | (1,398.20) | | (1,277.92) |

FIG. 11 (cont'd)

REFRIGERATION/COLD STORAGE FOOD SAFETY FILTERS

CROSS-REFERENCE TO RELATED APPLICATIONS

This nonprovisional application is a continuation of and claims priority to U.S. Provisional Patent Application No. 62/485,636, entitled "Cold Storage Filtration System", filed Apr. 14, 2017 by the same inventors, the entirety of which is incorporated herein by reference.

FIELD OF THE INVENTION

The present technology relates generally to air filtration systems, and, more particularly, to refrigeration food safety filters to improve the shelf life and food safety of perishable foods by reducing and or eliminating mold, bacteria, cross contamination and improper cold holding temperatures.

BACKGROUND OF THE INVENTION

Refrigeration, as used herein comprising both refrigerated cold storage (temperatures above 32° F.) and freezer storage (temperatures at or below 32° F.), is an integral part of the food products trade throughout the world. An estimated 30 percent of all food products consumed in developed countries are perishable, and as much as 20 percent of perishable product shipments arrive damaged by decay. Producers, wholesalers, distributors, and the ultimate users (whether the food service industry or the consumer) of the food products rely on refrigeration to maintain food safety and quality as the food products travel through distribution and sales sectors in the global economy. The food products industry spends perhaps hundreds of millions of dollars worldwide every year to ensure the integrity and wholesomeness of the food products. Considering that an estimated 4 million refrigerated cargo containers are shipped annually, the potential economic loss due to improper cold storage is tremendous.

Food products that require cold storage may be classified as potentially hazardous foods (PHF) as defined by U.S. Food and Drug Administration (FDA). Other regulatory bodies may use different terms, but all generally refer to food products that have a history of association with illness if the products are not properly temperature controlled. Such food products include dairy products (milk and milk products, eggs and egg products, produce (fruits and vegetables), meat and poultry, and fish and seafood.

Improper cold storage of these food products may promote the growth of pathogens, microorganisms, and toxins such as *E. coli, Salmonella, L. monocytogenes, Bacillus cereus, Staphylococcus aureus* and *Shigella*. In 1998, the FDA initiated a 10-year longitudinal study of 850 food service and retail food service establishments to investigate risk factors contributing to food borne illness outbreaks. The study was released in 2010, and the report was entitled: "The FDA Trend Analysis Report on the Occurrence of Foodborne Illness Risk Factors in Selected Institutional Foodservice, Restaurants, and Retail Food Store Facility Types (1998-2008)". Data was collected across 9 different establishments: hospitals; elementary schools; fast food restaurants; full-service restaurants; deli stores and departments, meat and poultry departments, seafood departments, and produce departments in grocery stores. Of the hospital facilities, the FDA conducted 483 observations in the "Improper Holding/Time & Temperature" category; and of those, 50 were out of compliance for holding food at 41 F or below, and 19 were out of compliance for cooling foods within 6 hours from 140 F to 41 F. Of the nursing homes facilities, they conducted 483 observations in the "Improper Holding/Time & Temperature" category; and of those, 21 were out of compliance for holding food at 41 F or below, and 23 were out of compliance for cooling foods within 6 hours from 140 F to 41 F. Of the elementary schools, they conducted 364 observations in the "Improper Holding/Time & Temperature" category; and of those, 27 were out of compliance for holding food at 41 F or below, and 3 were out of compliance for cooling foods within 6 hours from 140 F to 41 F. Of the fast food restaurants, they conducted 440 observations in the "Improper Holding/Time & Temperature" category; and of those, 70 were out of compliance for holding food at 41 F or below, and 11 were out of compliance for cooling foods within 6 hours from 140 F to 41 F. Of the full-service restaurants, they conducted 477 observations in the "Improper Holding/Time & Temperature" category; and of those, 69 were out of compliance for holding food at 41 F or below, and 33 were out of compliance for cooling foods within 6 hours from 140 F to 41 F. Of the delis and deli departments, they conducted 490 observations in the "Improper Holding/Time & Temperature" category; and of those, 59 were out of compliance for holding food at 41 F or below, and 14 were out of compliance for cooling foods within 6 hours from 140 F to 41 F. Of the meat and poultry departments, they conducted 156 observations in the "Improper Holding/Time & Temperature" category; and of those, 19 were out of compliance for holding food at 41 F or below. Of the seafood departments, they conducted 194 observations in the "Improper Holding/Time & Temperature" category; and of those 15 were out of compliance for holding food at 41 F or below. Of the produce departments, they conducted 248 observations in the "Improper Holding/Time & Temperature" category; and of those 50 were out of compliance for holding food at 41 F or below. Clearly, the FDA found that improper cold holding temperatures are a major problem across all facilities, and the causes can range from shippers propping open the doors to unload supplies to old equipment.

Cold storage is also just as integral in the distribution and sales of non-food products such as plants, fresh-cut flowers, biological/medical samples, health commodities such as medicines and medical supplies, and live animals. The total value of both the food and non-food cold chain supply industry is a 250-billion-dollar industry, that is expected to grow to over 270 billion in the next 4 years, and each product has its own unique needs and problems. For example, fresh-cut roses are susceptible to *Botrytis cinerea*, a necrotrophic fungus that can cause the petals to mold or rot, but it has no effect on food. So the industry is very diverse.

Whether a food product or a non-food product, some level of microorganism or contaminates will be present. The microorganisms and contaminates do lie dormant in the product, sometimes even under proper cold storage conditions. Each microorganism has its preferred temperature range for growth, as well as other environmental conditions such as humidity. Therefore, a cold storage temperature that may be effective for controlling the growth of one microorganism may have a negligible effect on another microorganism.

In addition, all food products in cold storage will decay to some extent. Ripening and/or decaying food products, particularly fruits and vegetables, can emit substantial amounts of methane, ethylene, and carbon dioxide gases. As the concentration of these gases builds within a cold storage unit (refrigerators and freezers), even as little as a few parts per million (ppm), the gases can promote accelerated decay in other food products within the cold storage unit (this is known as cross-contamination).

Humidity levels within the cold storage unit also play an important role in the rate of deterioration of food and non-food products. Higher humidity generally acts to accelerate deterioration caused by other factors. Higher humidity levels also promote mold, fungus and bacteria growth on surfaces within the cold storage unit. Excessive icing, snowing, and equipment deterioration can also be associated with high humidity levels in the cold storage unit, particularly in the presence of gaseous contaminates and acidic compounds.

To combat these cold storage issues, a number of products have been developed, such as sodium bicarbonate, potassium permanganate, calcium sulfate, calcium chloride, silica-gel, activated alumina, molecular sieves, zeolites, sodium aluminosilicates, potassium-calcium-sodium-aluminosilicate, cobalt chloride, pink hexaaquacobalt(ii) chloride, potassium sulfate, potassium chloride, sodium chloride, sodium sulfate, and sodium carbonate. While each of these products may have some use in solving cold storage problems, all of them are compounds with known toxicity levels. Owners, Executive Chefs and Operators of refrigeration units are reluctant to use products based on these compounds because of the potential for contamination of the fresh perishables. Since the health and lives of their customers are at stake, most owners and operators choose not to use these products and instead accept the problems related to cold storage.

Accordingly, what is needed are improved refrigeration food safety filters that not only stabilize temperatures by controlling the relative humidity, but also address the ripening and decaying issues that produce gases, molds, bacteria and toxic air. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure and explain various principles and advantages of those embodiments.

The devices, systems, and methods disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 11 depicts data of electrical bills of several stores tested with filters, according to an embodiment of the current invention.

DETAILED DESCRIPTION

Figure 1:
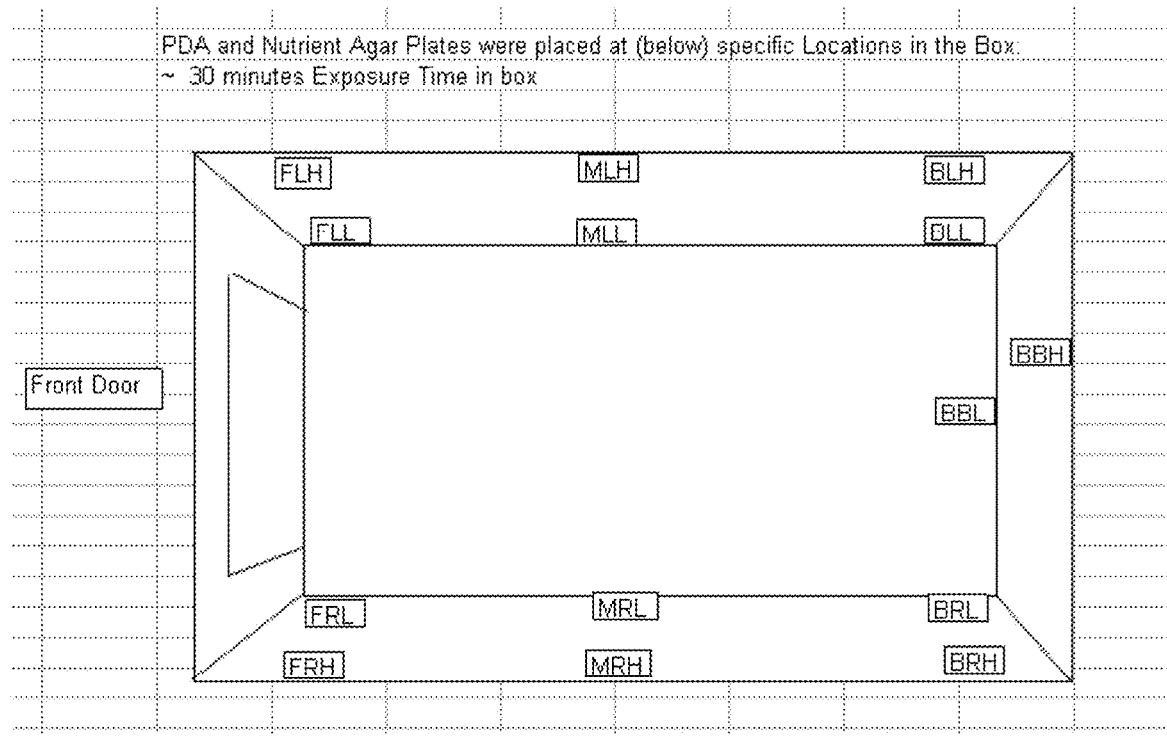
FIG. 1 is a schematic illustration of test PDA and Nutrient Agar Plates with Molds and Bacteria specific placement within a cold storage unit according to various embodiments.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology.

As such, some of the components may have been distorted from their actual scale for pictorial clarity.

In an embodiment, the current invention allows formation of systems and devices, hereinafter referred to generically as "filters," that solve drawbacks of conventional cold storage systems, as detailed above, with non-toxic food grade materials. Various embodiments of the filters of the present disclosure may be comprised of a base mineral, hygroscopic plant botanicals, and anti-bacterial plant botanicals. The mixture of these ingredients not only solved all of the cold storage problems discussed above, but surprisingly and unexpectedly allowed the cold storage units to operate at a lower temperature, reduced compressor run times, reduced defrost cycles, reduced power consumption, and reduced maintenance, all of which substantially reduced the operating cost of the cold storage units.

The term "effective amount" as used herein describes concentrations or amounts of components such as agents which are effective for producing an intended result, improving food safety by reducing micro-organisms, mold, mildew, fungi, viruses, bacteria and/or other harmful contaminates. Compositions according to the present invention may be used to effectuate a favorable change in levels of such harmful contaminates, whether that change is an improvement, relieving to some extent one or more of the conditions being treated, and/or that amount that will prevent, to some extent, one or more of the conditions that the target/area being treated has or is at risk of developing, or a complete cure of the condition itself.

The term "filter" as used herein is to be construed broadly. A filter according to certain embodiments may be in a semi-rigid bag or pouch with a mixture disposed therein, the bag or pouch being made of a substance that allows airborne moisture and contaminates to pass through. Additional filter embodiments may comprise a rigid frame of any desired shape and intended to retain the mixture therein. One skilled in the art will readily recognize that any desired shape or configuration of a filter capable of retaining the mixture therein is within the scope of the present disclosure.

Various embodiments of the base mineral may comprise a substance that has a honeycomb structure, low density, high porosity, high surface area, insulating properties, inertness, and adsorptive capacity. Certain embodiments of the base mineral may comprise diatoms. Many food processing operations, pharmaceuticals, and health and beauty products use diatoms, which attests to its acceptance in a food products environment. Diatoms may also kill microorganisms by a dehydration effect. The filtration abilities of diatoms may also remove gaseous contaminates. In various embodiments, the diatoms may comprise a particle size of 8-12 microns, although one skilled in the art will readily recognize that both larger and small particle sizes may be used, although effectiveness may vary.

The hygroscopic plant botanicals may comprise, according to various embodiments, flax fibers, coir, oat powder, coconut fiber, rye fiber, wheat fiber, bamboo fiber, or other U.S. Department of Agriculture (USDA) approved plant botanical by-products generally capable of adsorbing 100-300 percent of their weight in moisture. Various embodiments of the anti-bacterial plant botanicals may comprise blueberry fiber, cranberry coir or powder, caraway, celery, coriander, cilantro, tree barks, oils, echinacea, fava bean, lemon peel, orange peel, turmeric, grapefruit peel, papaya fiber, or other USDA approved plant, vegetable, herb, or fruit botanical having anti-bacterial properties. In various embodiments, the anti-bacterial plant botanicals may comprise fibers that clean and detoxify microbes that can be carried by airborne water vapor.

The base mineral may be prepared by grinding and sifting, or any other processes known in the art, to achieve the 8-12 micron particle size. The hygroscopic plant botanicals and the antibacterial plant botanicals may be dried and then cut, sliced, chopped, ground, or otherwise reduced in size. In various embodiments, the hygroscopic plant botanicals may be reduced to a particle size of about 30-400 microns, and the anti-bacterial plant botanicals may be reduced to a particle size of about 100-1000 microns. During preparation, including drying, the botanicals are maintained at a temperature less than about 120° F. to prevent degradation of the plant fibers. The diatoms and botanicals may be processed in their natural state without alteration with the exception of drying and size reduction.

After processing, the base mineral and botanicals may be uniformly mixed together. In various embodiments, the diatoms may comprise about 50-75 percent by weight, the hygroscopic plant botanicals may comprise about 10-30 percent by weight, and the anti-bacterial plant botanicals may comprise about 5-25 percent by weight. In certain embodiments, the mixture may contain about 62.5 percent by weight diatoms, about 25 percent by weight hygroscopic plant botanicals, and about 12.5 percent by weight anti-bacterial plant botanicals, or a ratio by weight of about 5:2:1. Other embodiments may comprise other ratios, although the specific effects on moisture content and retardation of spoilage may vary.

The mixture may then be placed in packaging that is FDA approved food grade material. The material may be porous enough to allow air, moisture, microorganisms, gaseous contaminates, and the like to readily pass through the material while containing the mixture without leaking. The material may also be non-dusting and non-tearing. In certain embodiments, the packaging may be bags made from Tyvek® material, a spunbonded olefin product produced by the E.I. DuPont de Nemours and Company. When a biodegradable packaging material is desired, Kraft paper is an acceptable alternative, although tearing strength may be reduced. One or more of the bags containing the mixture may be placed within the commercial refrigeration unit in a position where the bag will receive sufficient air flow. For example, the bags could be hung on a side of a shelving unit, on the interior walls, or simply placed on a shelf or other horizontal surface.

In certain embodiments, the mixture may be packaged in, for example a Tyvek bag, and then placed in a rigid rectangular frame similar to an air filter. In this embodiment, the frame filter may be placed internally near the air circulation system, or near the internal evaporator in the cold storage unit.

EXAMPLES

Example 1

A product trial was conducted at an operational facility of a major national restaurant chain. The purpose of the trial was to determine the performance of the filters of the present disclosure in a walk-in freezer, a walk-in cooler, and a reach-in cooler.

Walk-In Freezer

The walk-in freezer has a capacity of 1,848 ft$^3$, was about 13 years old, and the compressor and evaporator were about 13 years old. The freezer was used to store beef, chicken, fish, pork, vegetables, and ice cream. Initial conditions of the freezer included snowing and ice buildup on all interior surfaces. The set point of the freezer temperature control was set at −25° F. The ice buildup was so extensive that the door was difficult to close, which may lead to bending the door or damaging the hinges and door latch, leading to expensive repairs. Data were collected for about 1 week prior to installing the filters using an Aegis Temperature and Relative Humidity Monitor. The temperature ranged from −7.7° F. to −24.2° F., with an average of −19.6° F. The relative humidity ranged from 61% to 76.9%, with an average of 67.6%. Outside temperature averaged 64° F. and a relative humidity of 77%. During the initial one-week period, the electricity consumption of the freezer was measured with a Dent Elite Pro Logger. The daily average electricity consumption was 138.56 kWh. Filters were then installed in the freezer for a period of 6 months.

Over the test period, the filters eliminated snowing and ice buildup inside the freezer. Elimination of the ice buildup improved the overall efficiency of the cooling system by eliminating ice buildup on the evaporator, and recovery times after opening the door and entering the freezer were reduced. As a result of filter performance, the operating temperature of the freezer dropped to −25° F. without changing the set point. Due to the higher operating efficiency, the set point on the freezer was able to be increased from −25° to −10° F. The resulting daily average electricity consumption was 125.08 kWh, a 9.7% decrease in consumption. The electricity savings without changing the set point amount to $639 per year. Further electricity savings amounting to $989 per year were realized by raising the freezer set point to −10° F. Additional savings, estimated to be about $2,200, were realized from reduced inventory loss resulting from improved freezer conditions. Total savings were about $3,828. Although not measured during the test, it was expected that service calls for the freezer would be reduced as a result of more efficient operation.

Walk-In Cooler

The walk-in cooler had a capacity of 1,568 ft$^3$, was about 23 years old, and the compressor and evaporator were about 2 years old. The cooler was used to store produce, fruits, milk, cream, and eggs. Initial conditions of the cooler included dampness and a musty odor, with mold growing on the interior wall surfaces. Data were collected for about 1 week prior to installing the filters using an Aegis Temperature and Relative Humidity Monitor. The temperature ranged from 33.8° F. to 43° F., with an average of 37.7 F. The relative humidity ranged from 82.2% to 94.6%, with an average of 90.1%. Outside temperature averaged 64° F. and a relative humidity of 77%. Filters were then installed in the cooler for a period of 6 months.

Over the test period, the filters eliminated the musty odors and dampness. The mold on the walls was eliminated. The average temperature maintained in the cooler with the filters was 35.2° F., a drop of 2.5° F. or about 6.6%. No appreciable reduction in electricity consumption was observed because of the relatively new age of the cooling system (although cooling systems older than 3 years generally see a 10-18% decline in electricity consumption with the use of the filters) and the fact that ice does not build up on the cooling system of a cooler as it does on a freezer. Additional savings were realized from reduced inventory loss resulting from improved freezer conditions. Total estimated annual savings due to waste logs were about $4,200 without electricity savings. Although not measured during the test, it was expected that service calls for the coolers would be reduced as a result of more efficient operation by the equipment.

Reach-In Cooler

The reach-in cooler was located near the cook line and contained produce and other chilled items needed for immediate use on the cook line. Consequently, the reach-in cooler was in near constant use while the kitchen was operating. Over the test period, the average temperature maintained in the cooler with the filters was 36.4° F., a drop of 3.3° F. or about 8.3% from the average of 39.7° F. prior to using the filters. Relative humidity dropped from 77.3% to 75.8%, a drop of about 1.9%. Due to the lower power consumption of the small compressor motor, the electricity consumption was not measured.

Example 2

A Department of Defense sponsored study was conducted to assess the effect of the filters on mold and bacterial spores in a walk-in cooler. The cooler was initially emptied of food products and cleaned. The stored food products were replaced in the cooler and the cooler was allowed to equilibrate for 2 hours at 40° F. The baseline level of mold and bacteria within the cooler was determined. PDA plates (to measure mold) and nutrient agar plates (to measure bacteria) were placed throughout the cooler as illustrated in FIG. 1. Exposure time for the plates was 30 minutes. Table 1 lists the baseline results.

TABLE I

Baseline Mold and Bacterial Spore Results

| Placement in Cooler | PDA Plates (mold count) | Nutrient Agar Plates (bacterial count) |
|---|---|---|
| FLH | <1 | 9 (4 mold) |
| FLL | <1 | 1 |
| FRFI | 1 | 1 |
| FRL | <1 | 7 (1 mold) |
| MLH | 1 | 4 (1 mold) |
| MLL | 1 | 3 (1 mold) |
| MRH | 1 | 5 (2 mold) |
| MRL | <1 | 2 |
| BLH | <1 | 1 |
| BLL | <1 | 4 (1 mold) |
| BRH | 6 | 1 |
| BRL | 1 | <1 |
| BBH | <1 | 1 |
| BBL | <1 | 1 |
| Total | 11 | 40 |

Ten filters were then placed throughout the cooler along with the food products for a 5-week period. The PDA and nutrient agar plate test was repeated using the same placement within the cooler as for the baseline test. The results are presented in Table 2.

| Placement in Cooler | PDA Plates (mold count) | Nutrient Agar Plates (bacterial count) |
|---|---|---|
| FLH | <1 | <1 |
| FLL | <1 | <1 |
| FRH | <1 | <1 |
| FRI. | <1 | <1 |
| MLH | <1 | 1 |
| MLL | <1 | 1 |
| MRH | <1 | 1 |
| MRL | <1 | 1 |
| BLH | <1 | <1 |
| BLL | <1 | <1 |
| BRH | <1 | 1 |
| BRL | <1 | <1 |

-continued

| Placement in Cooler | PDA Plates (mold count) | Nutrient Agar Plates (bacterial count) |
|---|---|---|
| BBH | <1 | 1 |
| BBL | <1 | 1 |
| Total | <1 | 7 |

Figure 2:
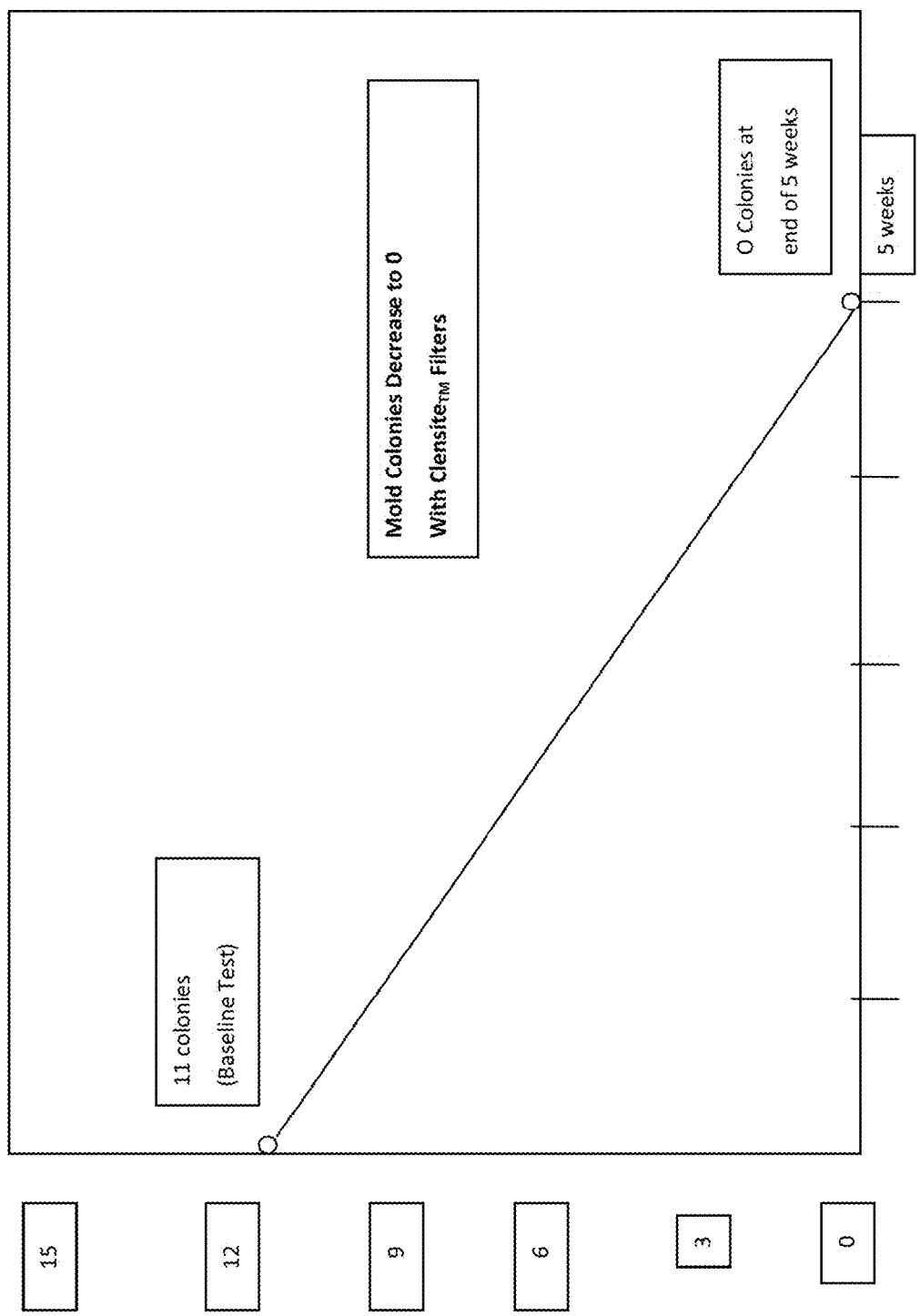
FIG. 2 is a graph of mold test data according to various embodiments.
Figure 3:
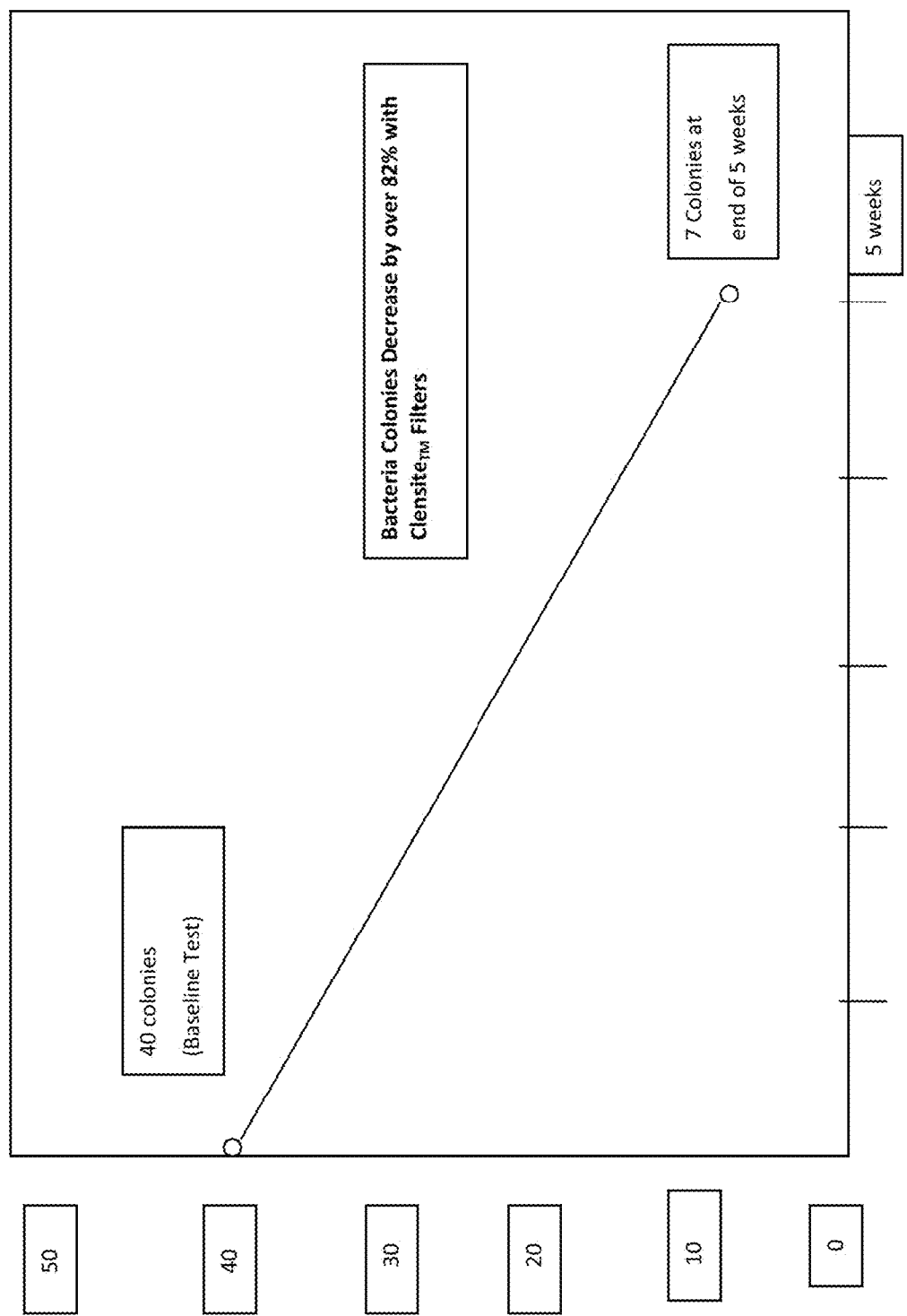
FIG. 3 is a graph of bacteria test data according to various embodiments.
Figure 4A:
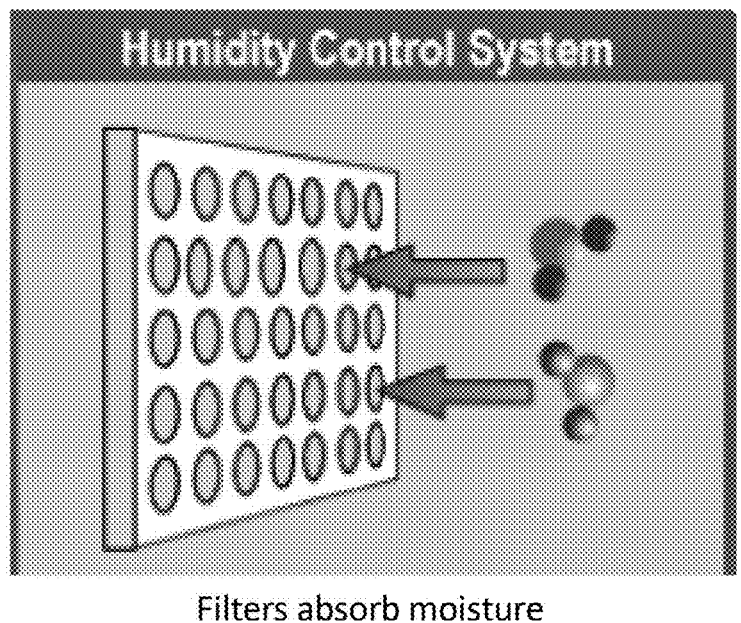
FIG. 4A is a schematic diagram illustrating moisture absorption by a filter according to various embodiments.
Figure 4B:
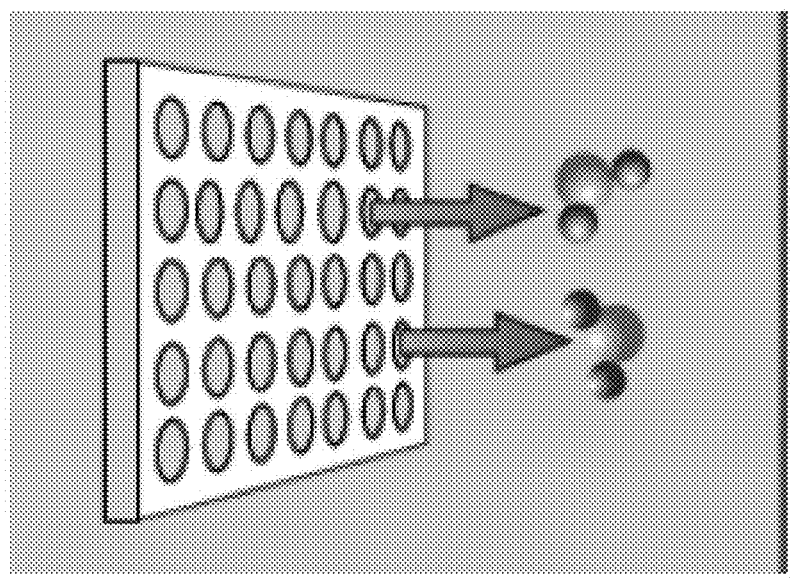
FIG. 4B is a schematic diagram illustrating moisture desorption by a filter according to various embodiments.

The mold and bacterial results are presented graphically in FIGS. 2 and 3, respectively, and illustrated that the filters stopped 100% all growth of mold and greatly reduced bacteria by 82% in the cooler. Additionally, before the filters were placed in the cooler, water was generally present in the drainage troughs. At the conclusion of the test period, no moisture was present anywhere inside the cooler. Compressor run time (minutes per day, which is a direct measure of electricity usage) was reduced by 7%.

Example 3

A Department of Defense sponsored study was conducted to evaluate potential shelf life extension of bananas with the use of the filters of the present disclosure for its Ethylene Detection and Control Tech Based Program. This test was two-fold. First it evaluated the effectiveness of this technology in eradicating ethylene, and second it evaluated the extension of the shelf life of bananas.

For testing purposes, two Polar King trailers were used. One of the trailers was packed with 5 filter panels, and the other without filters. Each trailer was loaded with bananas to simulate loading in either a Single Temp or Multi Temperature Refrigerated Container System.

Bananas are moderately sensitive to ethylene exposure. Most commercial cultivars of bananas require exposure to 100-150 ppm ethylene for 24-48 hours at 15-20° C. (59-68° F.) and 90-95% relative humidity to induce uniform ripening. Carbon dioxide concentration should be kept below 1% to avoid its effect on delaying ethylene action. Use of a forced-air system in ripening rooms assures more uniform cooling or warming of bananas as needed and more uniform ethylene concentration throughout the ripening.

The test setup consisted of a refrigerator (Polar King trailer) at 55° F. (with longer defrost cycles, to reduce excessive fluctuations in temperatures) to simulate ship board refrigerated temperatures, and 5 filter panels.

Figure 5:
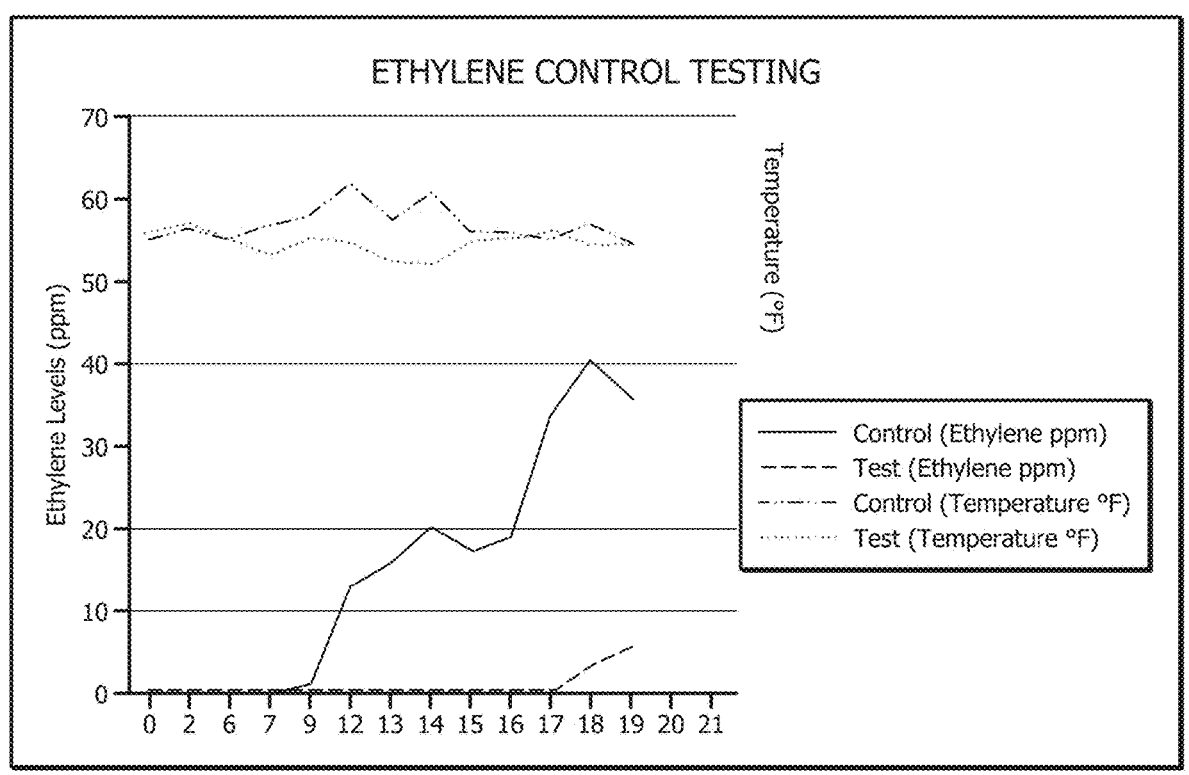
FIG. 5 is a graph of test data for ethylene control according to various embodiments.

A RAE Plus instrument was used to measure ethylene concentration, and a N9008 Thermometer was used to measure temperature. Measurements were taken in both the control trailer (without filters) and the trailer with the filters. Table 3 presents the recorded test date. FIG. 5 presents the test data graphically.

TABLE 3

Temperature and Ethylene Concentration Test Data

| Control Temperature (° F.) | Test Temperature (° F.) | Control Ethylene Concentration (ppm) | Test Ethylene Concentration (ppm) | Number of Days |
|---|---|---|---|---|
| 55.3 | 56 | 0 | 0 | 0 |
| 56.3 | 57 | 0 | 0 | 2 |
| 55.1 | 54.7 | 0 | 0 | 6 |
| 56.9 | 53 | 0 | 0 | 7 |
| 58.1 | 55.1 | 1.1 | 0 | 9 |
| 61.7 | 54.4 | 13.1 | 0 | 12 |
| 57.5 | 52.2 | 16.1 | 0 | 13 |
| 60.6 | 51.7 | 20.1 | 0.01 | 14 |
| 56 | 54.7 | 17.3 | 0 | 15 |
| 56 | 55 | 19 | 0 | 16 |
| 55 | 56 | 33.7 | 0 | 17 |
| 56.9 | 54.7 | 40.1 | 3.13 | 18 |
| 54.4 | 54.5 | 35.6 | 5.29 | 19 |

In FIG. 5, the growth of ethylene levels for the storage protocols is plotted. The storage temperature for bananas was maintained at 55° F. For the first nine days, the ethylene levels within the two protocols increased at the same rate; however, after day 9, the ethylene level in the control protocol increased, and the ethylene level in the Premier protocol remained negligible and showed a dramatic 85% reduction in ethylene levels between the two protocols. In fact, the control bananas resulted in a significant increase in brown spots on the skin. Increased ethylene levels resulted in *Fusarium roseum*, a kind of mold growth. Minor skin abrasions were also seen on the control protocol.

In order to keep ethylene concentrations at the appropriate level the container could not be opened regularly to see how the bananas were fairing. Thus, this test was more focused on the levels of ethylene that were being produced and the filter's ability to destroy it and less focused on the quality of bananas over time. That being said, the control was still opened about once a week just to make sure that the bananas were not completely spoiled, especially since the ethylene levels produced were higher than expected.

The data clearly showed that the filters were able to keep the ethylene concentrations lower than what was seen in the control. On average the ppm levels in the filter container were about 20 to 37 ppm lower than the levels in the control. Results clearly indicated the filter panels were effective in controlling the ethylene levels generated by banana containing containers. By controlling the ethylene, data suggested shelf life extension up to 19 days can be achieved for bananas.

Example 4

A test was conducted in 2017, by a National Casual Restaurant Chain, to determine the effectiveness of the filters on temperature and RH, in their Walk-in Coolers and Walk-in Freezers, in 10 of their locations. Temp Alert, a national temperature monitoring company, was hired to monitor the temperatures and RH in 2 of the 10 locations. The company collected a baseline of temperatures and RH, then installed the filters, and then continued to collect the temperatures and RH for another 90 days. The Walk-in Cooler temperatures showed dramatic improvements, as can be seen in Table 4. The decrease in temperatures ranged from over 5 F to 0.03 F. Additionally, the Walk-in Freezer showed dramatic improvements in the temperatures, as can be seen in Table 5. The decrease in temperatures was as much as 14 F.

TABLE 1

Temperature Comparisons of Before and After Filters in a National Casual Dining Restaurant Walk-in Cooler, Monitored by Temp Alert (11:00 pm-1:45 am)

| Reading Date | Reading Display | Reading Date | Reading Display | Difference |
|---|---|---|---|---|
| Jan. 3, 2017 11:00 PM | 43.9 | Mar. 1, 2017 11:01 PM | 38.1 | 5.8 |
| Jan. 3, 2017 11:05 PM | 43 | Mar. 1, 2017 11:06 PM | 38.1 | 4.9 |
| Jan. 3, 2017 11:10 PM | 42.3 | Mar. 1, 2017 11:11 PM | 38.1 | 4.2 |
| Jan. 3, 2017 11:15 PM | 41.2 | Mar. 1, 2017 11:16 PM | 38.3 | 2.9 |
| Jan. 3, 2017 11:20 PM | 40.3 | Mar. 1, 2017 11:21 PM | 38.5 | 1.8 |
| Jan. 3, 2017 11:25 PM | 39.4 | Mar. 1, 2017 11:26 PM | 38.5 | 0.9 |
| Jan. 3, 2017 11:30 PM | 38.8 | Mar. 1, 2017 11:31 PM | 38.5 | 0.3 |
| Jan. 3, 2017 11:35 PM | 39 | Mar. 1, 2017 11:36 PM | 38.5 | 0.5 |
| Jan. 3, 2017 11:40 PM | 39.4 | Mar. 1, 2017 11:41 PM | 38.7 | 0.7 |
| Jan. 3, 2017 11:45 PM | 39.9 | Mar. 1, 2017 11:46 PM | 38.7 | 1.2 |
| Jan. 3, 2017 11:50 PM | 40.3 | Mar. 1, 2017 11:51 PM | 38.8 | 1.5 |
| Jan. 3, 2017 11:55 PM | 40.8 | Mar. 1, 2017 11:56 PM | 38.8 | 2 |
| Jan. 4, 2017 12:00 AM | 41.2 | Mar. 2, 2017 12:01 AM | 39 | 2.2 |
| Jan. 4, 2017 12:05 AM | 41.5 | Mar. 2, 2017 12:06 AM | 39.2 | 2.3 |
| Jan. 4, 2017 12:10 AM | 42.1 | Mar. 2, 2017 12:11 AM | 39.4 | 2.7 |
| Jan. 4, 2017 12:15 AM | 42.3 | Mar. 2, 2017 12:16 AM | 39.4 | 2.9 |
| Jan. 4, 2017 12:20 AM | 42.6 | Mar. 2, 2017 12:21 AM | 39.4 | 3.2 |
| Jan. 4, 2017 12:25 AM | 43 | Mar. 2, 2017 12:26 AM | 39.4 | 3.6 |
| Jan. 4, 2017 12:30 AM | 43 | Mar. 2, 2017 12:31 AM | 39.6 | 3.4 |
| Jan. 4, 2017 12:35 AM | 43.3 | Mar. 2, 2017 12:36 AM | 39.7 | 3.6 |
| Jan. 4, 2017 12:40 AM | 43.5 | Mar. 2, 2017 12:41 AM | 39.7 | 3.8 |
| Jan. 4, 2017 12:45 AM | 43.7 | Mar. 2, 2017 12:46 AM | 40.1 | 3.6 |
| Jan. 4, 2017 12:50 AM | 43.9 | Mar. 2, 2017 12:51 AM | 40.1 | 3.8 |
| Jan. 4, 2017 12:55 AM | 44.1 | Mar. 2, 2017 12:56 AM | 40.1 | 4 |
| Jan. 4, 2017 1:00 AM | 44.2 | Mar. 2, 2017 1:01 AM | 40.1 | 4.1 |
| Jan. 4, 2017 1:05 AM | 44.2 | Mar. 2, 2017 1:06 AM | 40.3 | 3.9 |
| Jan. 4, 2017 1:10 AM | 44.4 | Mar. 2, 2017 1:11 AM | 40.3 | 4.1 |
| Jan. 4, 2017 1:15 AM | 44.4 | Mar. 2, 2017 1:16 AM | 40.6 | 3.8 |
| Jan. 4, 2017 1:20 AM | 44.8 | Mar. 2, 2017 1:21 AM | 40.6 | 4.2 |
| Jan. 4, 2017 1:25 AM | 44.8 | Mar. 2, 2017 1:26 AM | 40.6 | 4.2 |
| Jan. 4, 2017 1:30 AM | 44.8 | Mar. 2, 2017 1:31 AM | 40.8 | 4 |
| Jan. 4, 2017 1:35 AM | 44.4 | Mar. 2, 2017 1:36 AM | 40.8 | 3.6 |
| Jan. 4, 2017 1:40 AM | 43.5 | Mar. 2, 2017 1:41 AM | 40.8 | 2.7 |
| Jan. 4, 2017 1:45 AM | 42.3 | Mar. 2, 2017 1:46 AM | 41 | 1.3 |

TABLE 2

Temperature Comparisons of Before and After Filters in a National Casual Restaurant Chain Freezer, Monitored by Temp Alert (11:22 am-1:57 pm)

| Reading Date | Reading Display | Reading Date | Reading Display | Difference |
|---|---|---|---|---|
| Jan. 3, 2017 11:22 | 8.6 | Feb. 3, 2017 11:22 | 2.8 | 5.8 |
| Jan. 3, 2017 11:27 | 12.6 | Feb. 3, 2017 11:27 | 4.6 | 8 |
| Jan. 3, 2017 11:32 | 16.3 | Feb. 3, 2017 11:32 | 6.6 | 9.7 |
| Jan. 3, 2017 11:37 | 20.1 | Feb. 3, 2017 11:37 | 8.4 | 11.7 |
| Jan. 3, 2017 11:42 | 23.5 | Feb. 3, 2017 11:42 | 10.2 | 13.3 |
| Jan. 3, 2017 11:47 | 25.9 | Feb. 3, 2017 11:47 | 11.8 | 14.1 |
| Jan. 3, 2017 11:52 | 25.3 | Feb. 3, 2017 11:52 | 13.6 | 11.7 |
| Jan. 3, 2017 11:57 | 21.4 | Feb. 3, 2017 11:57 | 14 | 7.4 |
| Jan. 3, 2017 12:02 | 17.2 | Feb. 3, 2017 12:02 | 11.1 | 6.1 |
| Jan. 3, 2017 12:07 | 13.8 | Feb. 3, 2017 12:07 | 7.7 | 6.1 |
| Jan. 3, 2017 1212 | 11.1 | Feb. 3, 2017 12:12 | 4.8 | 6.3 |
| Jan. 3, 2017 12:17 | 8.8 | Feb. 3, 2017 12:17 | 2.7 | 6.1 |
| Jan. 3, 2017 12:22 | 7 | Feb. 3, 2017 12:22 | 1 | 6 |
| Jan. 3, 2017 12:27 | 5.5 | Feb. 3, 2017 12:27 | −0.4 | 5.9 |
| Jan. 3, 2017 12:32 | 4.3 | Feb. 3, 2017 12:32 | −1.5 | 5.8 |
| Jan. 3, 2017 12:37 | 3.2 | Feb. 3, 2017 12:37 | −2.4 | 5.6 |
| Jan. 3, 2017 12:42 | 2.5 | Feb. 3, 2017 12:42 | −1.5 | 4 |
| Jan. 3, 2017 12:47 | 2.1 | Feb. 3, 2017 12:47 | 1 | 1.1 |
| Jan. 3, 2017 12:52 | 3 | Feb. 3, 2017 12:52 | 0 | 3 |
| Jan. 3, 2017 12:57 | 2.8 | Feb. 3, 2017 12:57 | −1.7 | 4.5 |
| Jan. 3, 2017 13:02 | 2.1 | Feb. 3, 2017 13:02 | −2.6 | 4.7 |
| Jan. 3, 2017 13:07 | 1.6 | Feb. 3, 2017 13:07 | −0.2 | 1.8 |
| Jan. 3, 2017 13:12 | 2.1 | Feb. 3, 2017 13:12 | 0.7 | 1.4 |
| Jan. 3, 2017 13:17 | 2.5 | Feb. 3, 2017 13:17 | −1.1 | 3.6 |
| Jan. 3, 2017 13:22 | 1.9 | Feb. 3, 2017 13:22 | −2.6 | 4.5 |
| Jan. 3, 2017 13:27 | 1.2 | Feb. 3, 2017 13:27 | −0.6 | 1.8 |
| Jan. 3, 2017 13:32 | 1.8 | Feb. 3, 2017 13:32 | 0.9 | 0.9 |
| Jan. 3, 2017 13:37 | 2.3 | Feb. 3, 2017 13:37 | −0.8 | 3.1 |
| Jan. 3, 2017 13:42 | 1.8 | Feb. 3, 2017 13:42 | −2.6 | 4.4 |
| Jan. 3, 2017 13:47 | 1.6 | Feb. 3, 2017 13:47 | −0.8 | 2.4 |
| Jan. 3, 2017 13:52 | 1 | Feb. 3, 2017 13:52 | 1 | 0 |
| Jan. 3, 2017 13:57 | 1.4 | Feb. 3, 2017 13:57 | −0.6 | 0 |

Example 5

A test was conducted to determine the effectiveness of the filters to reducing aging of roses in a shipping container in cold storage. A standard floral shipping container containing 250 roses was shipped from Ecuador (4 days shipping time). After receipt of the shipping container, a filter containing 3 oz. of material was placed in the center of the shipping container without unpacking the roses. The shipping container with the roses still inside was placed in cold storage for another 7 days. The roses were removed from cold storage and inspected. Only 3 roses had slight discoloration on the guard petals. Once the guard petals were removed the roses were perfectly normal. The rose stems were clipped, and the roses were hydrated. The roses were compared to roses with just 4 days in cold storage. Both were displayed for 7 days and there was no distinction between the two groups.

It was theorized that when excess moisture is wicked away by the filter, condensation/water vapor from the guard petals, packaging materials and shipping box botrytis spores are reduced or eliminated from forming on the product. The filter did not dry out or damage the roses. Because the filters reduce mold and mildew by capturing spores, positive results were seen in transport and storage.

Example 6

Acetic Acid and Ethylene Absorption

A test was conducted to evaluate the ability of the filters to remove acetic acid and ethylene gas from a refrigeration unit. The filter comprised a cloth bag containing approximately 0.9 kg (2.0 lbs) of absorbent material. The cloth bag was contained in a plastic holder (approximately 40 cm×30 cm×2.2 cm) designed to allow free airflow through the bag of absorbent. The filter was installed at ceiling level in the refrigeration unit.

Acetic acid (vinegar) may be used in dilute form for cleaning in refrigeration units storing vegetable foods and flowers. Odors from the cleaning agent may be absorbed by the food and flower products. In addition, certain products that contain vinegar such as salad dressings, marinades and other food sauces may be stored in open containers in the refrigeration unit.

Ethylene is a colourless gas with a faint sweetish smell. It is produced naturally by a variety of fruits, vegetables, and flowering plants, and plays a role in regulating their growth and development. Ethylene gas is commonly used to trigger ripening in some crops after they have been picked. When ethylene gas is applied to select fruits and vegetables at a controlled rate, ripening times can be controlled so that the produce is "ready to eat" when it sold to consumers. Similarly, decreasing ethylene gas concentrations (naturally released by produce and from sources such as combustion engine exhaust) can prolong shelf life by slowing the aging process (e.g., ripening time, bloom life).

Test Equipment

Mirian 1B.

The Miran 1B (Foxboro, Mass.) is an infrared spectrophotometer that can be used to monitor airborne concentrations of a variety of chemical compounds. For this test procedure, the Miran 1B was set up to analyze for ethylene gas in accordance with the operation manual for the instrument. The instrument was zeroed before the beginning of each test. The sampling probe for the Miran 1B was placed in the middle of a glove box through the sampling port.

Glove Box.

The glove box used for this procedure was 17 ft$^3$ in size. The glove box was equipped with a sliding, sealable door that leads to a small (1 ft$^3$) access chamber. The smaller access chamber contained a second, sealable door that lead to the outside environment. The glove box was also equipped with an external sampling port to which the Miran analyser was attached by tubing.

Filter.

The filter comprised 130 g of material.

Other Equipment.

A lab stand and clamp was used to hold the end of Miran 1B sampling probe in position in the middle of the main chamber of the glove box. A fan was used to generate continuous air mixing inside the glove box. A plastic tray was used to hold the filter.

Test Method—

Ethylene Gas Absorption. The Miran 1B was zeroed before each test and the air in the glove box was sampled to ensure that there was no residue from previous tests. Once the Miran 1B was properly warmed up and ready to sample, a sealed bag of filter material was placed into the glove box. A Tedlar bag filled with ethylene gas and fitted with a sampling septum and a gas syringe were placed inside the test chamber. The entry ports to the glove box were then sealed shut. Inside the glove box, the syringe was used to remove controlled quantities of ethylene from the Tedlar bag and then discharged in front of the fan to get an even concentration of gas throughout the space. Tests were conducted with ethylene gas concentrations in the 10-20 ppm range. Once the target concentration was reached the supply of ethylene gas and the syringe were removed from the glove box by way of the small chamber through the first sealed door. Once ethylene gas concentrations were stabilized, the bag of filter material was opened and poured into a plastic tray which was located on the bottom, middle of the glove box. Concentration readings were taken every 15 minutes initially, and then less frequently as ethylene gas concentrations declined slowly. The concentration of ethylene gas was monitored for 24 hours, at which time the test was terminated. In addition to flushing air from the glove box between tests, one test was conducted per day to ensure the glove box was sufficiently vented to remove residual gas from the previous test.

Test Method—Acetic Acid Absorption.

The Miran 1B was zeroed before each test and the air in the glove box was sampled to ensure that there was no residue from previous tests. Once the Miran 1B was properly warmed up and ready to sample, a sealed bag of filter material was placed into the glove box as well as a sealed bottle of concentrated acetic acid and a cloth. The glove box was then sealed shut. Inside the glove box, the bottle of acetic acid was opened and a small amount was poured onto the cloth. The cloth was then placed in front of the fan, resulting in the evaporation of the acetic acid into the air inside the glove box. Once the concentration of acetic acid inside the glove box was between 5 to 10 ppm, the bottle of acetic acid and the cloth were removed from the glove box by way of the small chamber outside the first sealed door. The bag of filter material was then opened and poured into a plastic tray and placed on the bottom of the chamber, in the middle of the glove box. Concentration readings were taken every minute for the first 15 minutes and approximately every five minutes thereafter until the concentration of airborne acetic acid was no longer detectable. In addition to venting the chamber between tests, one test was conducted per day to ensure the glove box was sufficiently vented to remove residual vapour from the previous test.

Test Equipment

A climate-controlled room equipped with an internal air conditioning unit was selected for conducting the tests. This room had the following physical characteristics:

Size: 7.8 ft high×12.3 ft. wide×13.2 ft long

Volume: 1270 ft$^3$

Relative Humidity: Approximately 50%

Temperature: Approximately 15° C.

Results

Figure 6:
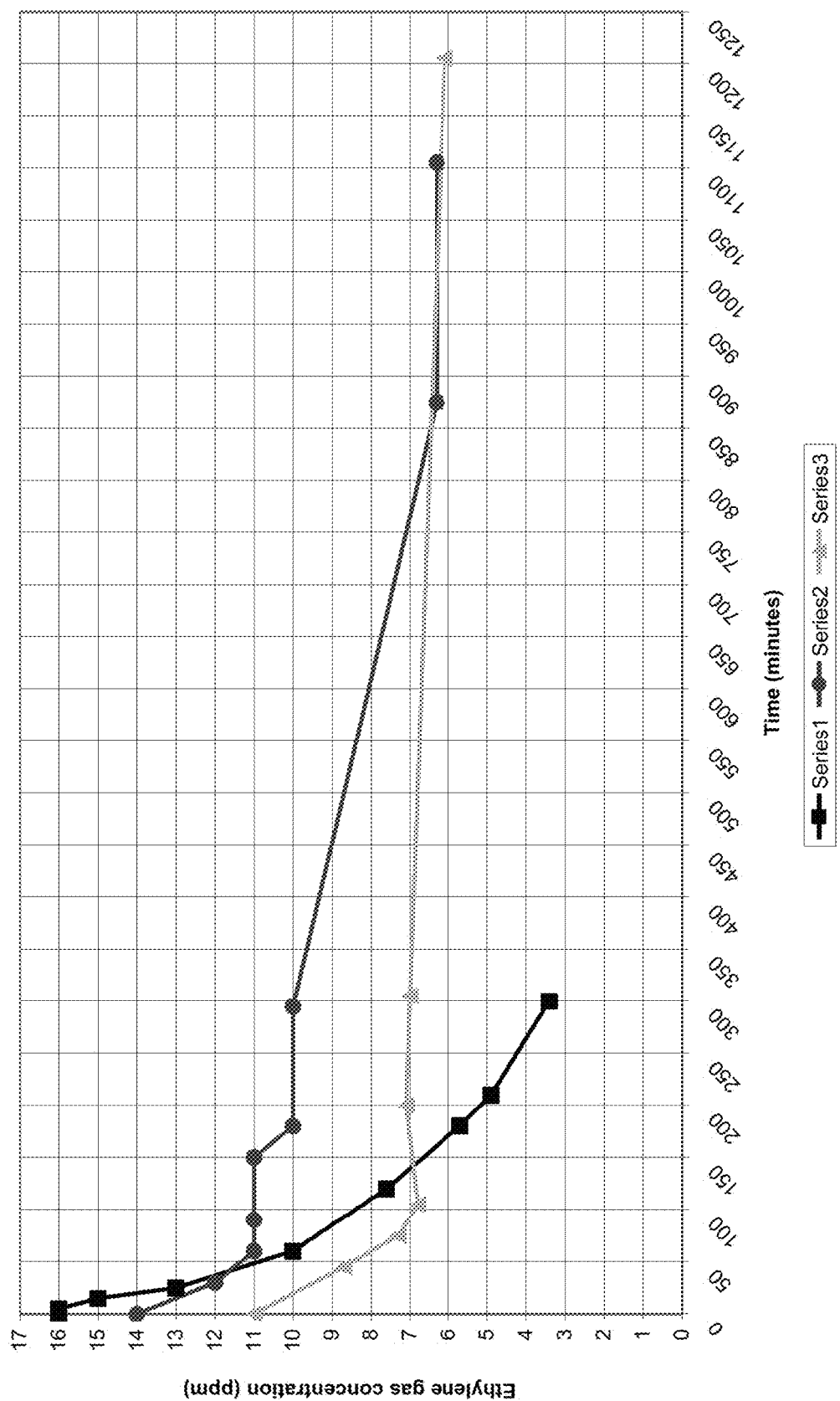
FIG. 6 is a graph of test date for ethylene control according to various embodiments.

FIG. 6 presents the results of the three tests showing filter absorption of ethylene gas. The results of all three ethylene gas absorption tests indicate that the filter panels absorbed ethylene gas, however, the rate of absorption and total amount absorbed was found to vary between the three tests. Table 6 summarizes the results.

TABLE 4

Test Results for Filter Panel Absorption of Ethylene Gas

| Trial Number | Time to Achieve X % of Initial Ethylene Gas Concentration | | Percentage of Ethylene Gas Absorbed |
|---|---|---|---|
| | 75% Remaining | 50% Remaining | |
| 1 | ~40 min. | ~120 min. | 79% |
| 2 | ~175 min. | ~775 min. | 55% |
| 3 | ~60 min. | >1200 min. | 45% |
| Average | ~92 min. | ~698 min. | 60% |

Figure 7:
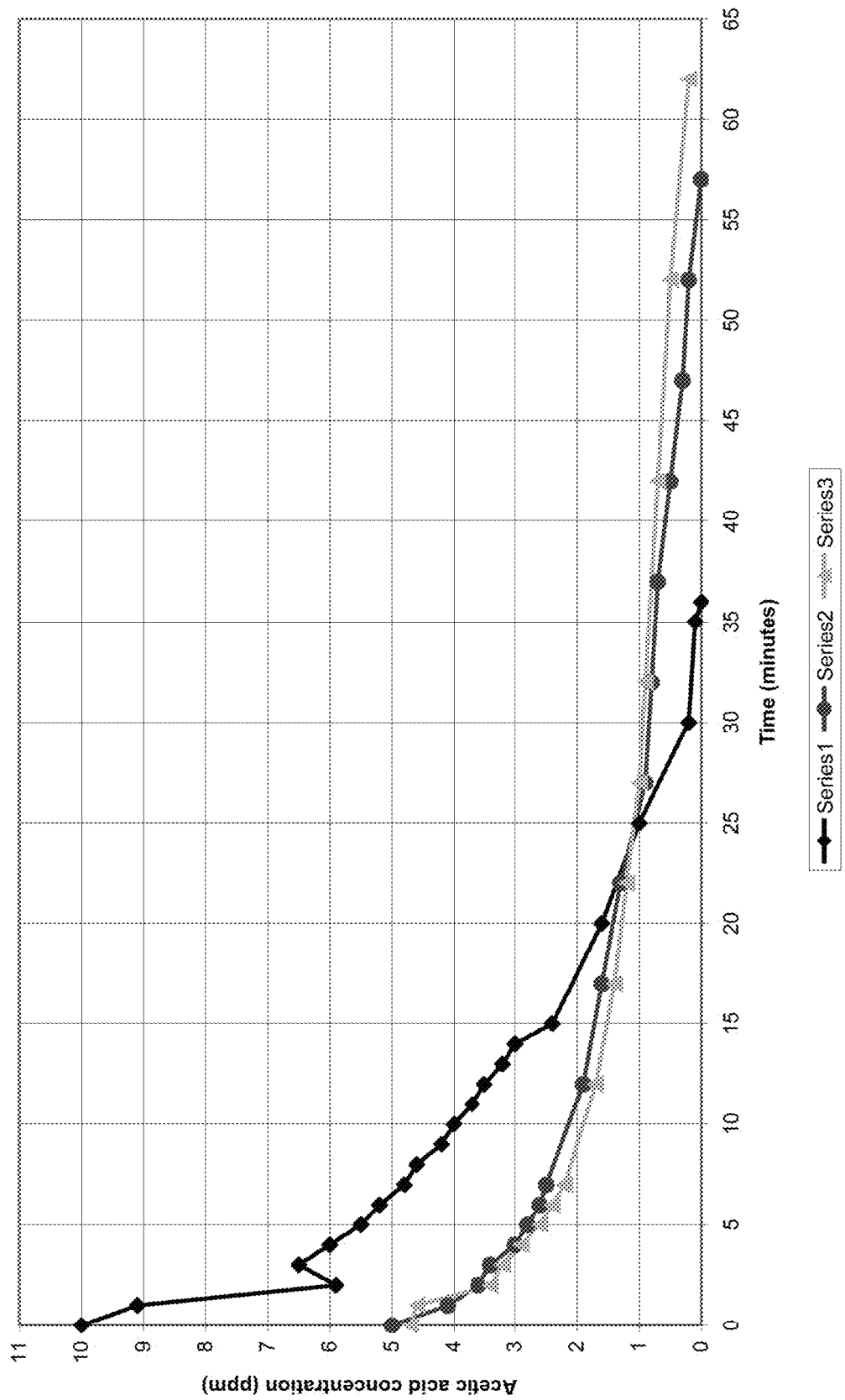
FIG. 7 is a graph of test date for acetic acid control according to various embodiments.
Figure 8:
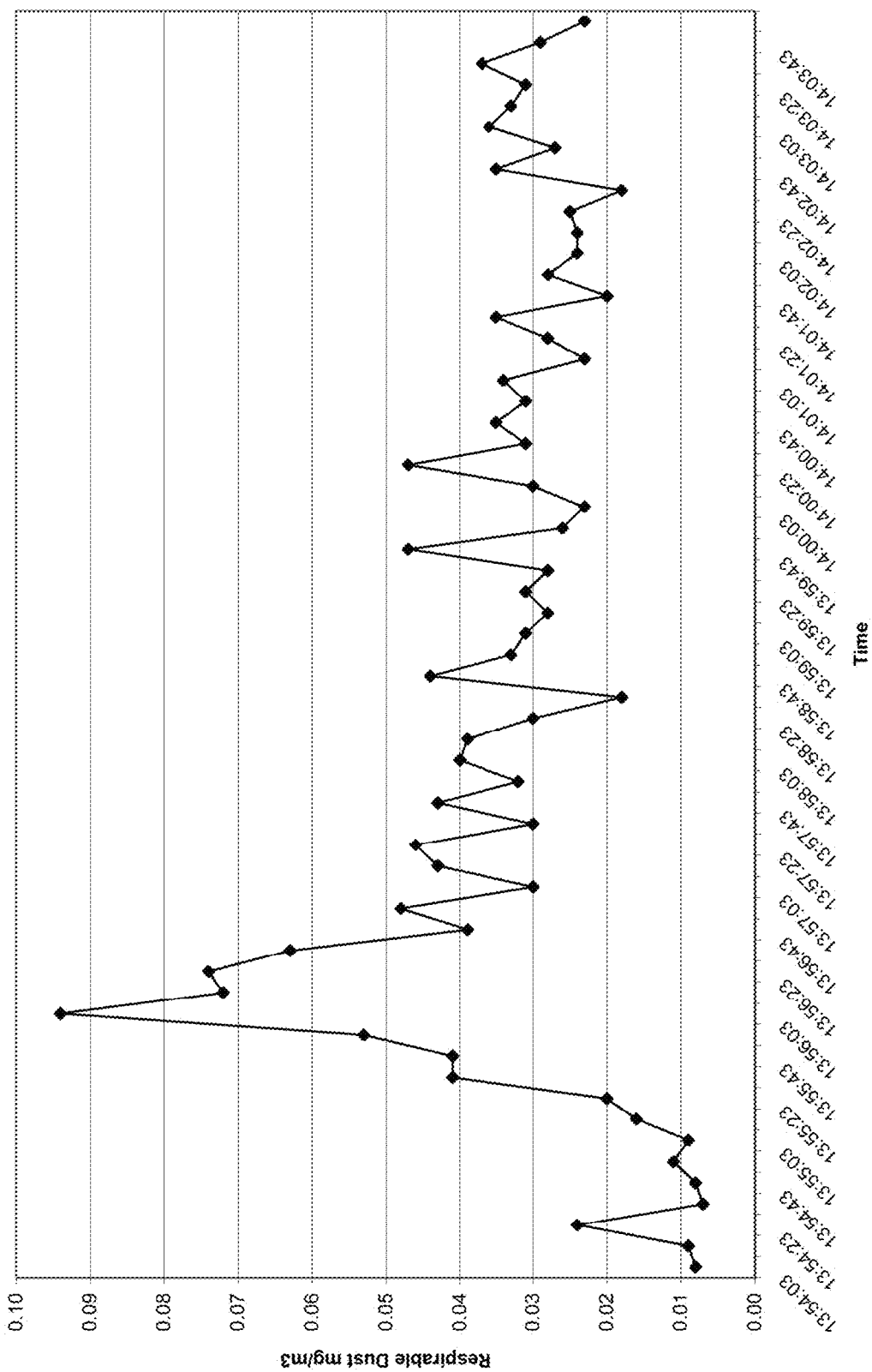
FIG. 8 is a graph of test data for generation of respirable dust according to various embodiments.
Figure 9:
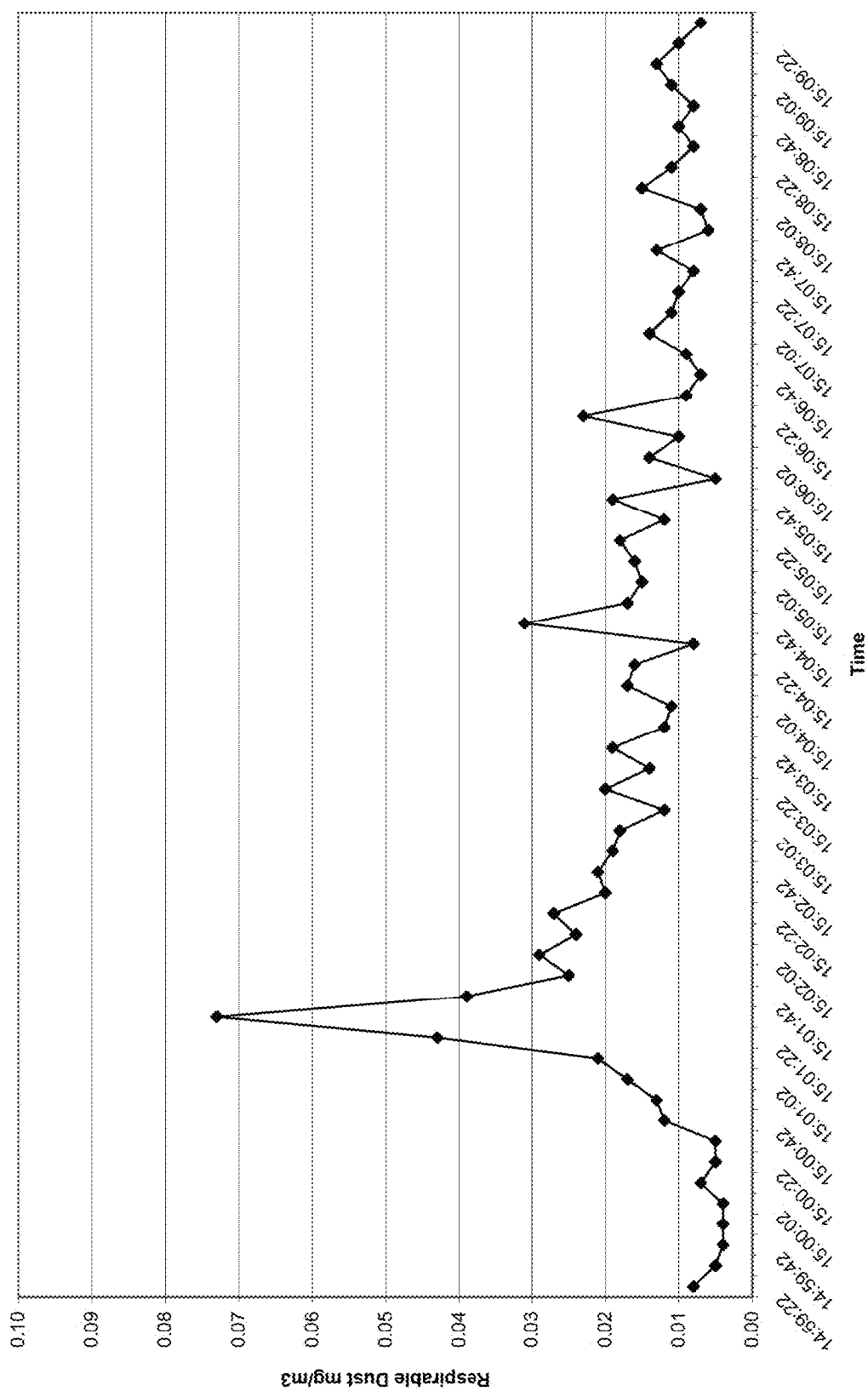
FIG. 9 is a graph of test data for generation of respirable dust according to various embodiments.

FIG. 7 presents the results of the three tests showing filter absorption of acetic acid.

TABLE 5

Test Results for Filter Panel Absorption of Acetic Acid Vapor

| Trial Number | Time to Achieve X % of Initial Acetic Acid Concentration | | | Percentage of Acetic Acid Absorbed |
|---|---|---|---|---|
| | 75% Remaining | 50% Remaining | 25% Remaining | |
| 1 | ~1.5 min. | ~6.5 min. | ~14.5 min. | 100% |
| 2 | ~1.5 min. | ~7 min. | ~23 min. | 100% |
| 3 | ~1.5 min. | ~6.5 min. | ~23 min. | 96% |
| Average | ~1.5 min. | ~6.7 min. | ~20.2 min. | 98.6% |

CONCLUSIONS

The results of the gas absorption tests indicate that the filter panels absorb both ethylene gas and acetic acid. The tests results show that airborne acetic acid is absorbed rapidly and completely (approximately 20 minutes for >96% absorption). In contrast, ethylene gas is absorbed at a slower rate. The amount of ethylene gas absorbed was also found to vary. On average a 60% reduction in ethylene gas concentrations was measured after 24 hours.

It should be noted that the above test was conducted with an early experimental version of the filter panels. Subsequently developed filter panels have shown significant improvements in absorption characteristics (greater than 300% improvement in moisture absorption).

Example 7

Figure 10:
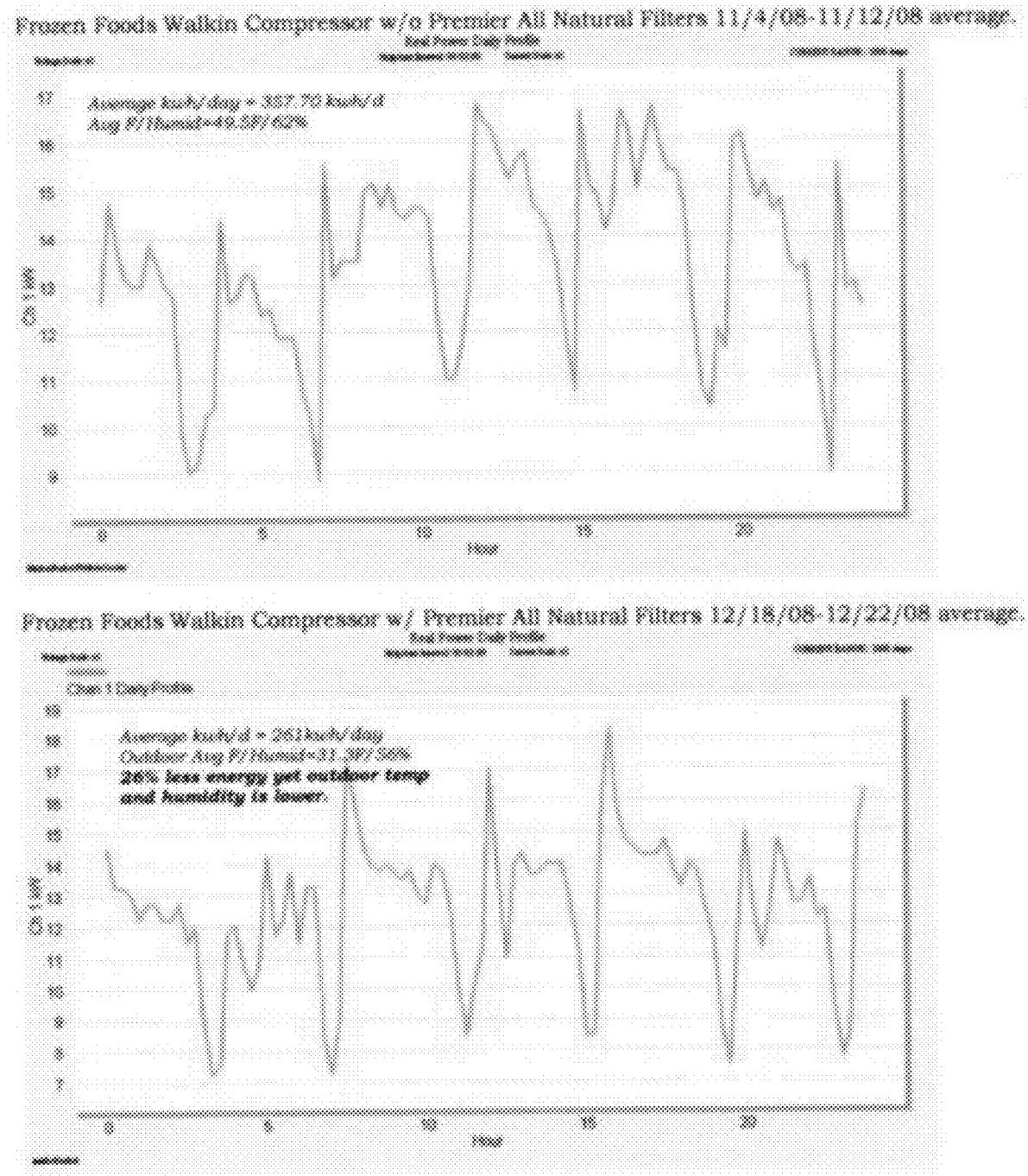
FIG. 10 depicts KWH usage within a walk-in freezer with and without use of filters, according to an embodiment of the current invention.

Public Services of New Hampshire tested the effects of the filters on the use of energy, in a Nashua, N.H., grocery store Walk-in Freezer. The freezer without filters used 357.70 Kwh/d (per day) compared to the freezer with filters which used 261 Kwh/d (per day), resulting in a 96.7 Kwh/d savings per day, which was a 26% reduction in KWH. See FIG. 10.

Example 8

In 2005, a National Casual Dining Restaurant Chain, with over 600+ locations, compared the year-to-year differences in electric bills, in 13 Tampa stores with the filters in their walk-in coolers. The total electric bill for each store included all the energy costs to power the entire store and the age of the stores ranged from very old stores with various equipment being replaced to a newer store with most equipment still under warranty. Additionally, the stores spanned multiple power grids with dramatically different KWH costs. However, even with all those uncontrolled variables, 9 of the 13 stores showed a power savings that ranged from $1612.00 over 5 months ($322.40 per month) to $46.88 over 5 months ($9.38 per month). The most accurate and predictive measure of energy savings of all the stores, was determined to be store #13, because of its newer and under warranty equipment, and it had a savings of $1398.20 over 5 months ($279.64 per month). FIG. 11 includes the 13 stores and their electrical bills.

Example 9

In this test, a National Chain Restaurant monitored the energy saving in one of their St. Petersburg stores. The average amps used in the freezer decreased from 14.20 to 8.6 (39.4% reduction) and in the cooler from 5.4 to 4.4 (18.5% reduction). It was also determined that between 12 noon and 4 pm before the filter installation in the walk-in cooler, the average temperature was 43.4 F, the average RH was 97%, and in that 4-hour period there were 34 alarms indicating temperatures were exceeding 42° F. After the filters were installed, the average temperature dropped to 39.2° F., the average RH dropped to 89.5%, and there was only 1 alarm during that 4-hour peak traffic period indicating temperatures in excess of 42° F. The same analysis of the midnight to 4 am time (when supplies were delivered) showed the average temperature before filters was 40.6° F., the average RH was 94%, and there were 10 alarms indicating temperatures were exceeding 42° F. The average temperature with filters declined to 37.9° F. during that same time period, the RH dropped to 90.9%, and the alarms indicating temperatures over 42° F. dropped to zero.

Example 10

In this study, an EMSL Method M009 was conducted, including swabbing, culturing and counting the 5 most prominent types of bacteria found. The first swab (May 24, 2017) found a total count of 103,600,000 CFUs, on the walls and the back of the evaporator, of 6 different bacteria species (see also Table 8):
 1. *Bacillus marisflavi*
 2. *Bacillus pumills/safensis*
 3. *Paenibacillus* sp.
 4. *Bacillus cereus/thuringiensis*
 5. *Elizabethakingia* sp.
 6. *Empedobacter* sp.

TABLE 8

| Sample Description | Location | Media | Temp (C) | Sample Measure (Swab) | Analytical Sensitivity (CFU/Swab) | Dilution | Bacteria Identification | Colony Count | CFUs (CFU/Swab) |
|---|---|---|---|---|---|---|---|---|---|
| Sample 1 | Prep Cooler-Walls | TSAB | 35 | 1 | 100,000 | 100000 | *Bacillus marisflavi* | 43 | 4,300,000 |
|  |  |  |  |  | 100,000 | 100000 | *Bacillus pumilus/safensis* | 4 | 400,000 |
|  |  |  |  |  | 100,000 | 100000 | *Paenibacillus* sp. | 4 | 400,000 |
|  |  |  |  |  |  |  | Total | 51 | 5,100,000 |
| 341704606-001 |  |  |  |  |  |  |  |  |  |
| Sample 2 | Prep Cooler-EVAP | TSAB | 35 | 1 | 10,000 | 10000 | *Bacillus cereus/thuringiensis* | 6 | 60,000 |
|  |  |  |  |  | 100,000 | 100000 | *Elizabethkingia* sp. | 577 | 57,700,000 |
|  |  |  |  |  | 100,000 | 100000 | *Empedobacter* sp. | 407 | 40,700,000 |
|  |  |  |  |  |  |  | Total | 990 | 98,500,000 |
| 341704606-002 |  |  |  |  |  |  |  |  |  |

No discernible blank was submitted with this group of samples

*Bacillus cereus* was the greatest concern. It is a Gram-positive, spore-forming microorganism capable of causing foodborne disease, that comes from the intestines of insects. The second swab (Aug. 11, 2017) found only 5,650,000 CFUs, which represented a 94.5% decrease. The following is a list of the 5 bacteria cultured (see also Table 9):
 1. *Staphylococcus epidemidis*
 2. *Bacillus marisflavi*
 3. *Bacillus pumilus/safensis*
 4. *Bacillus* sp.
 5. *Micrococcus yunnanensis*

TABLE 9

| Sample Description | Location | Media | Temp (C) | Sample Measure (Swab) | Analytical Sensitivity (CFU/Swab) | Dilution | Bacteria Identification | Colony Count | CFUs (CFU/Swab) |
|---|---|---|---|---|---|---|---|---|---|
| Sample 1 | Prep Cooler- Walls | TSAB | 35 | 1 | 10,000 | 10000 | *Staphylococcus epidermidis* | 27 | 270,000 |
| | | | | | | | Total | 27 | 270,000 |
| 341707152-001 | | | | | | | | | |
| Sample 2 | Prep Cooler- EVAP | TSAB | 35 | 1 | 10,000 | 10000 | *Bacillus marisflavi* | 43 | 430,000 |
| | | | | | 10,000 | 10000 | *Bacillus pumilus/safensis* | 185 | 1,850,000 |
| | | | | | 10,000 | 10000 | *Bacillus* sp. | 6 | 60,000 |
| | | | | | 10,000 | 10000 | *Micrococcus yunnanensis* | 35 | 350,000 |
| | | | | | | | Total | 269 | 2,690,000 |
| 341707152-002 | | | | | | | | | |

No discernible blank was submitted with this group of samples

As can be seen, *Bacillus cereus* was no longer detected. Nothing else was done to the commercial cooler between May 24, 2017 to Aug. 11, 2017 (including cleaning). *Bacillus* sp. only had 54% of the markers for *Bacillus Cereus*.

While the present technology has been described in connection with a series of preferred embodiments, these descriptions are not intended to limit the scope of the technology to the particular forms set forth herein. It will be further understood that the methods of the technology are not necessarily limited to the discrete steps or the order of the steps described. To the contrary, the present descriptions are intended to cover such alternatives, modifications, and equivalents as may be included within the spirit and scope of the technology as defined by the appended claims and otherwise appreciated by one of ordinary skill in the art.

What is claimed is:

1. A filter for reducing airborne contaminants, airborne moisture, or a combination thereof in a cold storage unit comprising:

a packaging comprised of a porous material; and a mixture contained within the packaging comprising between about 50-75% w/w diatoms;

between about 20-30% w/w dried hygroscopic plant botanicals;

and between about 10-15% w/w dried antibacterial plant botanicals;

wherein the dried hygroscopic plant botanicals are selected from the group consisting of flax fibers, coconut fibers, oat powder, rye fiber, wheat fiber, bamboo fiber and combinations thereof, wherein the dried antibacterial plant botanicals are selected from the group consisting of blueberry fiber, cranberry powder, caraway, celery, coriander, cilantro, tree bark, echinacea, fava bean, lemon peel, orange peel, grapefruit peel, turmeric, papaya fiber and combinations thereof;

wherein the mixture contains the diatoms, the hygroscopic plant botanicals and the antibacterial plant botanicals in a weight ratio of 5:2:1;

wherein the porous material of the packaging is an FDA-approved food grade material selected from the group consisting of a flashspun material of high density polyethylene fibers and kraft paper;

wherein the packaging is in the form of a bag or pouch capable of containing the mixture in an interior of the bag or pouch;

wherein the porous material of the packaging allows airborne contaminants and airborne moisture to pass through the porous material while preventing the mixture from leaking out of the porous material of the packaging.

2. The filter of claim 1, wherein the airborne contaminants are bacteria, fungi, viruses or gaseous contaminants.

3. The filter of claim 1, wherein the diatoms are between about 8 to 12 microns in size.

4. The filter of claim 1, wherein the hygroscopic plant botanicals are reduced to a particle size of between about 30 to 400 microns.

5. The filter of claim 1, wherein the antibacterial plant botanicals are reduced to a particle size of between about 100-1000 microns.

6. The filter of claim 1, further comprising a frame into which the packaging is placed.

7. The filter of claim 1, wherein the porous material is non-dusting and non-tearing.

8. A method of reducing airborne contaminants, airborne moisture, or a combination thereof in a cold storage unit comprising:

providing a packaging comprised of a porous material;

mixing a plurality of diatoms, hygroscopic plant botanicals, and antibacterial plant botanicals to form a mixture comprising between about 50-75% w/w of the plurality of diatoms;

between about 20-30 w/w of the hygroscopic plant botanicals wherein the hygroscopic plant botanicals are selected from the group consisting of flax fibers, coconut fibers, oat powder, rye fiber, wheat fiber, bamboo fiber and combinations thereof, and between about 10-15% w/w of the antibacterial plant botanicals wherein the antibacterial plant botanicals are selected from the group consisting of blueberry fiber, cranberry powder, caraway, celery, coriander, cilantro, tree bark, echinacea, fava bean, lemon peel, orange peel, grapefruit peel, turmeric, papaya fiber and combinations thereof, placing the mixture into the packaging to form a filter wherein the mixture is fully contained within the packaging;

placing the filter in the cold storage unit;

and allowing air containing airborne moisture and contaminants to flow through the filter containing the mixture;

wherein the mixture removes or reduces the airborne contaminants, airborne moisture, or the combination thereof in the cold storage unit by entrapment within the mixture contained in the filter, wherein the mixture contains the plurality of diatoms, the hygroscopic plant botanicals and the antibacterial plant botanicals in a weight ratio of 5:2:1;

wherein the porous material of the packaging is an FDA-approved food grade material selected from the group consisting of a flashspun material of high density polyethylene fibers and kraft paper; and wherein the packaging is in the form of a bag or pouch.

9. The method of claim 8, wherein the hygroscopic plant botanicals and the antibacterial plant botanicals are maintained at a temperature less than 120° F. during preparation.

10. The method of claim 8, further comprising cutting or grinding the dried hygroscopic plant botanicals and the antibacterial plant botanicals prior to placement in the packaging.

11. The method of claim 10, wherein the hygroscopic plant botanicals are cut or grinded to obtain particles between about 30 to 400 microns in size.

12. The method of claim 10, wherein the antibacterial plant botanicals are cut or grinded to obtain particles between about 100 to 1000 microns in size.

13. The method of claim 8, further comprising grinding the diatoms to between about 8 to 12 microns in size.

14. The method of claim 8, wherein the filter is placed in the cold storage unit near an air circulation system or internal evaporator.

15. The method of claim 8, wherein the porous material is non-dusting and non-tearing.

16. The method of claim 8, wherein the airborne contaminants are bacteria, fungi, viruses or gaseous contaminants.

* * * * *